United States Patent
Madden et al.

(10) Patent No.: US 12,358,993 B2
(45) Date of Patent: *Jul. 15, 2025

(54) METHODS FOR THE TREATMENT OF THYROID EYE DISEASE

(71) Applicant: Horizon Therapeutics Ireland DAC, Dublin (IE)

(72) Inventors: David Madden, Mount Kisco, NY (US); Kathleen Gabriel, Voorhees, NJ (US); Guido Magni, Basel (CH); Richard Woodward, Phoenixville, PA (US); Shao-Lee Lin, Lake Forest, IL (US); Jeffrey W. Sherman, Lincolnshire, IL (US)

(73) Assignee: HORIZON THERAPEUTICS IRELAND DAC, Dublin (IE)

( * ) Notice: Subject to any disclaimer, the term of this patent is extended or adjusted under 35 U.S.C. 154(b) by 462 days.

This patent is subject to a terminal disclaimer.

(21) Appl. No.: 17/531,368

(22) Filed: Nov. 19, 2021

(65) Prior Publication Data

US 2022/0340667 A1 Oct. 27, 2022

Related U.S. Application Data

(63) Continuation of application No. 16/293,293, filed on Mar. 5, 2019, now Pat. No. 11,208,490.

(60) Provisional application No. 62/638,689, filed on Mar. 5, 2018.

(51) Int. Cl.
| | |
|---|---|
| C07K 16/28 | (2006.01) |
| A61K 9/00 | (2006.01) |
| A61K 9/08 | (2006.01) |
| A61K 9/19 | (2006.01) |
| A61K 39/00 | (2006.01) |
| A61K 39/395 | (2006.01) |
| A61K 45/06 | (2006.01) |
| A61K 47/18 | (2017.01) |
| A61K 47/26 | (2006.01) |
| A61P 27/02 | (2006.01) |
| C07K 16/24 | (2006.01) |

(52) U.S. Cl.
CPC ........ C07K 16/2863 (2013.01); A61K 9/0019 (2013.01); A61K 9/08 (2013.01); A61K 9/19 (2013.01); A61K 39/3955 (2013.01); A61K 45/06 (2013.01); A61K 47/183 (2013.01); A61K 47/26 (2013.01); A61P 27/02 (2018.01); C07K 16/241 (2013.01); C07K 16/248 (2013.01); C07K 16/2887 (2013.01); *A61K 2039/505* (2013.01); *A61K 2039/54* (2013.01); *A61K 2039/545* (2013.01); *C07K 2317/21* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,572,897 B2 | 8/2009 | Graus et al. | |
| 7,579,157 B2 | 8/2009 | Graus et al. | |
| 8,153,121 B2 | 4/2012 | Smith et al. | |
| 11,208,489 B2 | 12/2021 | Madden et al. | |
| 11,208,490 B2 | 12/2021 | Madden et al. | |
| 12,209,130 B2 | 1/2025 | Madden et al. | |
| 2007/0218514 A1 | 9/2007 | Smith et al. | |
| 2016/0287611 A1 | 10/2016 | Dobak | |
| 2019/0225696 A1 | 7/2019 | Madden et al. | |
| 2019/0270820 A1 | 9/2019 | Madden et al. | |
| 2021/0284741 A1 | 9/2021 | Madden et al. | |
| 2022/0324985 A1 | 10/2022 | Madden et al. | |
| 2022/0356257 A1 | 11/2022 | Sherman et al. | |
| 2024/0301072 A1 | 9/2024 | Madden et al. | |

FOREIGN PATENT DOCUMENTS

| | | |
|---|---|---|
| WO | WO-2016064716 A1 | 4/2016 |
| WO | WO-2019173352 A1 | 9/2019 |

OTHER PUBLICATIONS

Bahn, RS, "Current Insights into the Pathogenesis of Graves' Ophthalmopathy", Horm Metab Res. 47(10):773-8 (2015).
Bahn, RS, "Graves' ophthalmopathy", N Engl J Med. 362:726-38 (2010).
Bartelena, L, et al. "Efficacy and safety of three different cumulative doses of intravenous methylprednisolone for moderate to severe and active Graves' orbitopathy", J Clin Endocrinol Metab. 97(12):4454-63 (2012).
Chen, H, et al., "Teprotumumab, an IGF-1R blocking monoclonal antibody inhibits TSH and IGF-1 action in fibrocytes", J Clin Endocrinol Metab. 99:E1635-40 (2014).
Chen, H, et al., Sichuan Da Xue Xue Bao Yi Xue Ban. 48(5):727-731 (2017).

(Continued)

*Primary Examiner* — Ruixiang Li
(74) *Attorney, Agent, or Firm* — Knobbe Martens Olson & Bear LLP

(57) ABSTRACT

The invention provides a method of treating or reducing the severity of thyroid-associated ophthalmopathy (TAO), also known as thyroid eye disease (TED) or Graves' ophthalmopathy or orbitopathy (GO), or a symptom or aspect thereof, in subjects that have undergone prior treatment for TAO, TED, or GO, and either did not respond to said prior treatment or relapsed after said prior treatment. The invention also provides antibodies, or antigen binding fragments thereof, and pharmaceutical compositions useful in the disclosed methods.

39 Claims, No Drawings
Specification includes a Sequence Listing.

(56) References Cited

OTHER PUBLICATIONS

Clinical Trials No. NCT01868997. Teprotumumab (RV 001) Treatment in Patients With Active Thyroid Eye Disease, Version 1. Reported date submitted: May 30, 2013. Date publicly available: Unknown. Date accessed: May 24, 2024. Available at https://classic.clinicaltrials.gov/ct2/history/NCT01868997?V_1=View#StudyPageTop.
Clinical Trials No. NCT01868997. Teprotumumab (RV 001) Treatment in Patients With Active Thyroid Eye Disease, Version 2. Reported date submitted: Jun. 9, 2013. Date publicly available: Unknown. Date accessed: May 24, 2024. Available at https://classic.clinicaltrials.gov/ct2/history/NCT01868997?V_2=View#StudyPageTop.
Clinical Trials No. NCT01868997. Teprotumumab (RV 001) Treatment in Patients With Active Thyroid Eye Disease, Version 3. Reported date submitted: Jun. 13, 2013. Date publicly available: Unknown. Date accessed: May 24, 2024. Available at: https://classic.clinicaltrials.gov/ct2/history/NCT01868997?V_3=View#StudyPageTop.
Clinical Trials No. NCT01868997. Teprotumumab (RV 001) Treatment in Patients With Active Thyroid Eye Disease, Version 4. Reported date submitted: Jun. 21, 2013 Date publicly available: Unknown. Date accessed: May 24, 2024. Available at: https://classic.clinicaltrials.gov/ct2/history/NCT01868997?V_4=View#StudyPageTop.
Clinical Trials No. NCT01868997. Teprotumumab (RV 001) Treatment in Patients With Active Thyroid Eye Disease, Version 5. Reported date submitted: Jun. 27, 2013. Date publicly available: Unknown. Date accessed: May 24, 2024. Available at: https://classic.clinicaltrials.gov/ct2/history/NCT01868997?V_5=View#StudyPageTop.
Clinical Trials No. NCT01868997. Teprotumumab (RV 001) Treatment in Patients With Active Thyroid Eye Disease, Version 6. Reported date submitted: Aug. 9, 2013. Date publicly available: Unknown. Date accessed: May 24, 2024. Available at: https://classic.clinicaltrials.gov/ct2/history/NCT01868997?V_6=View#StudyPageTop.
Clinical Trials No. NCT01868997. Teprotumumab (RV 001) Treatment in Patients With Active Thyroid Eye Disease, Version 7. Reported date submitted: Sep. 12, 2013. Date publicly available: Unknown. Date accessed: May 24, 2024. Available at: https://classic.clinicaltrials.gov/ct2/history/NCT01868997?V_7=View#StudyPageTop.
Clinical Trials No. NCT01868997. Teprotumumab (RV 001) Treatment in Patients With Active Thyroid Eye Disease, Version 8. Reported date submitted: Jan. 20, 2014. Date publicly available: Unknown. Date accessed: May 24, 2024. Available at: https://classic.clinicaltrials.gov/ct2/history/NCT01868997?V_8=View#StudyPageTop.
Clinical Trials No. NCT01868997. Teprotumumab (RV 001) Treatment in Patients With Active Thyroid Eye Disease, Version 9. Reported date submitted: Mar. 17, 2014. Date publicly available: Unknown. Date accessed: May 24, 2024. Available at: https://classic.clinicaltrials.gov/ct2/history/NCT01868997?V_9-View#StudyPageTop.
Clinical Trials No. NCT01868997. Teprotumumab (RV 001) Treatment in Patients With Active Thyroid Eye Disease, Version 10. Reported date submitted: Apr. 16, 2014. Date publicly available: Unknown. Date accessed: May 24, 2024. Available at: https://classic.clinicaltrials.gov/ct2/history/NCT01868997?V_10=View#StudyPageTop.
Clinical Trials No. NCT01868997. Teprotumumab (RV 001) Treatment in Patients With Active Thyroid Eye Disease, Version 11. Reported date submitted: Jul. 29, 2014. Date publicly available: Unknown. Date accessed: May 24, 2024. Available at: https://classic.clinicaltrials.gov/ct2/history/NCT01868997?V_11=View#StudyPageTop.
Clinical Trials No. NCT01868997. Teprotumumab (RV 001) Treatment in Patients With Active Thyroid Eye Disease, Version 12. Reported date submitted: Nov. 3, 2014. Date publicly available: Unknown. Date accessed: May 24, 2024. Available at: https://classic.clinicaltrials.gov/ct2/history/NCT01868997?V_12=View#StudyPageTop.
Clinical Trials No. NCT01868997. Teprotumumab (RV 001) Treatment in Patients With Active Thyroid Eye Disease, Version 13. Reported date submitted: Nov. 13, 2014. Date publicly available: Unknown. Date accessed: May 24, 2024. Available at: https://classic.clinicaltrials.gov/ct2/history/NCT01868997?V_13=View#StudyPageTop.
Clinical Trials No. NCT01868997. Teprotumumab (RV 001) Treatment in Patients With Active Thyroid Eye Disease, Version 14. Reported date submitted: Feb. 5, 2015. Date publicly available: Unknown. Date accessed: May 24, 2024. Available at: https://classic.clinicaltrials.gov/ct2/history/NCT01868997?V_14=View#StudyPageTop.
Clinical Trials No. NCT01868997. Teprotumumab (RV 001) Treatment in Patients With Active Thyroid Eye Disease, Version 15. Reported date submitted: Mar. 6, 2015. Date publicly available: Unknown. Date accessed: May 24, 2024. Available at: https://classic.clinicaltrials.gov/ct2/history/NCT01868997?V_15=View#StudyPageTop.
Clinical Trials No. NCT01868997. Teprotumumab (RV 001) Treatment in Patients With Active Thyroid Eye Disease, Version 16. Reported date submitted: Sep. 18, 2015. Date publicly available: Unknown. Date accessed: May 24, 2024. Available at: https://classic.clinicaltrials.gov/ct2/history/NCT01868997?V_16=View#StudyPageTop.
Clinical Trials No. NCT01868997. Teprotumumab (RV 001) Treatment in Patients With Active Thyroid Eye Disease, Version 17. Reported date submitted: Oct. 3, 2016. Date publicly available: Unknown. Date accessed: May 24, 2024. Available at: https://classic.clinicaltrials.gov/ct2/history/NCT01868997?V_17=View#StudyPageTop.
Clinical Trials No. NCT01868997. Teprotumumab (RV 001) Treatment in Patients With Active Thyroid Eye Disease, Version 18. Reported date submitted: Nov. 15, 2016. Date publicly available: Unknown. Date accessed: May 24, 2024. Available at: https://classic.clinicaltrials.gov/ct2/history/NCT01868997?V_18=View#StudyPageTop.
Clinical Trials No. NCT01868997. Teprotumumab (RV 001) Treatment in Patients With Active Thyroid Eye Disease, Version 19. Reported date submitted: Nov. 23, 2016. Date publicly available: Unknown. Date accessed: May 24, 2024. Available at: https://classic.clinicaltrials.gov/ct2/history/NCT01868997?V_19=View#StudyPageTop.
Clinical Trials No. NCT01868997. Teprotumumab (RV 001) Treatment in Patients With Active Thyroid Eye Disease, Version 20. Reported date submitted: Mar. 20, 2017. Date publicly available: Unknown. Date accessed: May 24, 2024. Available at: https://classic.clinicaltrials.gov/ct2/history/NCT01868997?V_20=View#StudyPageTop.
Clinical Trials No. NCT01868997. Teprotumumab (RV 001) Treatment in Patients With Active Thyroid Eye Disease, Version 21. Reported date submitted: Aug. 10, 2017. Date publicly available: Unknown. Date accessed: May 24, 2024. Available at: https://classic.clinicaltrials.gov/ct2/history/NCT01868997?V_21=View#StudyPageTop.
Clinical Trials No. NCT01868997. Teprotumumab (RV 001) Treatment in Patients With Active Thyroid Eye Disease, Version 22. Reported date submitted: Mar. 27, 2018. Date publicly available: Unknown. Date accessed: May 24, 2024. Available at: https://classic.clinicaltrials.gov/ct2/history/NCT01868997?V_22=View#StudyPageTop.
Douglas, R., et al., "Aberrant expression of the insulin-like growth factor-1 receptor by T cells from patients with Graves' disease may carry functional consequences for disease pathogenesis", J Immunol. 178(5):3281-7 (2007).
Douglas, R., et al., "B cells from patients with Graves' disease aberrantly express the IGF-1 receptor: implications for disease pathogenesis", J Immunol. 181(8):5768-74 (2008).

(56) References Cited

OTHER PUBLICATIONS

Douglas, R., et al., "Increased generation of fibrocytes in thyroid-associated ophthalmopathy", J Clin Endocrinol Metab. 95(1):430-8 (2010).
Ezra, DG, et al., ARVO Annual Meeting Scientific Abstracts (2011).
Gianoukakis, AG, et al., "Immunoglobulin G from patients with Graves' disease induces interleukin-16 and RANTES expression in cultured human thyrocytes: a putative mechanism for T-cell infiltration of the thyroid in autoimmune disease", Endocrinology 147(4):1941-9 (2006).
Görtz, GE, et al., "Pathogenic Phenotype of Adipogenesis and Hyaluronan in Orbital Fibroblasts From Female Graves' Orbitopathy Mouse Model", Endocrinology 157(10):3771-3778 (2016).
Hoa, N, et al., "Nuclear Targeting of IGF-1 Receptor in Orbital Fibroblasts from Graves' Disease: Apparent Role of ADAM17", PLoS One. 7(4):e34173 (2012).
Hwang, CJ, et al., "Orbital fibroblasts from patients with thyroid-associated ophthalmopathy overexpress CD40: CD154 hyperinduces IL-6, IL-8, and MCP-1", Invest Ophthalmol Vis Sci. 50(5):2262-8 (2009).
Khong, JJ, et al., "Pathogenesis of thyroid eye disease: review and update on molecular mechanisms", Br J Ophthalmol. 100(1):142-50 (2016).
Khoo, TK, et al., "Pathogenesis of Graves' Ophthalmopathy: The Role of Autoantibodies", Thyroid 17(10):1013-1018 (2007).
Krieger, CC, et al., "Thyroid Stimulating Hormone (TSH)/Insulin-like Growth Factor 1 (IGF1) Receptor Cross-talk in Human Cells", Curr Opin Endocr Metab Res, 2:29-33 (2018).
Krieger, CC, et al., "TSH/IGF-1 Receptor Cross-Talk Rapidly Activates Extracellular Signal-Regulated Kinases in Multiple Cell Types", Endocrinology 158(10):3676-3683 (2017).
Krieger, CC, et al., "TSHR/IGF-1R Cross-Talk, Not IGF-1R Stimulating Antibodies, Mediates Graves' Ophthalmopathy Pathogenesis", Thyroid 27(5):746-747 (2017).
Kumar, S, et al., J Clin Endocrinol Metab. 97(5):1681-7 (2012).
Kumar, S, et al., Thyroid 25(10):1145-50 (2015).
Lovell, D. J. et al., "Adalimumab with or without Methotrexate in Juvenile Rheumatoid Arthritis", N Engl J Med Aug. 2008, vol. 359, pp. 810-820.
Ma, H. et al., "The Adverse Events Profile of Anti-IGF-IR Monoclonal Antibodies in Cancer Therapy", Br J Clin Pharmacol., 77(6):917-28, (2013).
Marcus-Samuels, B, et al., Thyroid 28(5):650-655 (2018).
Naik, VM, et al., "Immunopathogenesis of thyroid eye disease: emerging paradigms", Surv Ophthalmol. 55(3):215-26 (2010).
Pawlowski, P, et al., "Decreased Frequencies of Peripheral Blood CD4+CD25+CD127-Foxp3+ in Patients with Graves' Disease and Graves' Orbitopathy: Enhancing Effect of Insulin Growth Factor-1 on Treg Cells", Horm Metab Res. 49(3):185-191 (2017).
Place, RF, et al., "Inhibiting thyrotropin/insulin-like growth factor 1 receptor crosstalk to treat Graves' ophthalmopathy: studies in orbital fibroblasts in vitro", Br J Pharmacol. 174(4):328-340 (2017).
Pritchard, J, et al., "Igs from patients with Graves' disease induce the expression of T cell chemoattractants in their fibroblasts", J Immunol. 168(2):942-50 (2002).
Pritchard, J, et al., "Immunoglobulin activation of T cell chemoattractant expression in fibroblasts from patients with Graves' disease is mediated through the insulin-like growth factor I receptor pathway", J Immunol. 170(12):6348-54 (2003).
Salvi, M., "Immunotherapy for Graves' ophthalmopathy", Curr Opin Endocrinol Diabetes Obes. 21(5):409-14 (2014).
Salvi, M., et al., "Efficacy of B-cell targeted therapy with rituximab in patients with active moderate to severe Graves' orbitopathy: a randomized controlled study", J Clin Endocrinol Metab. 100(2):422-31 (2015).
Smith, T, et al., "Building the Case for Insulin-Like Growth Factor Receptor-I Involvement in Thyroid-Associated Ophthalmopathy", Front Endocrinol (Lausanne) 7:167 (2017).
Smith, T, et al., "Insulin-Like Growth Factor-I Regulation of Immune Function: A Potential Therapeutic Target in Autoimmune Diseases?", Pharmacological Rev. 62(2):199-236 (2010).
Smith, T, et al., "Pathogenesis of Graves' orbitopathy: A 2010 update", J Endocrinol Invest. 33(6):414-21 (2010).
Smith, T, et al., "Unique attributes of orbital fibroblasts and global alterations in IGF-1 receptor signaling could explain thyroid-associated ophthalmopathy", Thyroid. 18(9):983-8 (2008).
Smith, T, et al., Best Pract Res Clin Endocrinol Metab. 26(3):291-302 (2012).
Smith, T, et al., Nat Rev Endocrinol. 11(3):171-181 (2015).
Song, D, et al., "Locally produced insulin-like growth factor-1 by orbital fibroblasts as implicative pathogenic factor rather than systemically circulated IGF-1 for patients with thyroid-associated ophthalmopathy", Graefes Arch Clin Exp Ophthalmol. 250(3):433-40 (2012).
Stan, MN, et al., "Randomized controlled trial of rituximab in patients with Graves' orbitopathy", J Clin Endocrinol Metab. 100(2):432-41 (2015).
Terwee, C. B. et al., "Development of a disease specific quality of life questionnaire for patients with Graves' ophthalmopathy: the GO-QOL", Br J Ophthalmopathy, 1998, vol. 82, pp. 773-779.
Tsui, S, et al., "Evidence for an association between thyroid-stimulating hormone and insulin-like growth factor 1 receptors: a tale of two antigens implicated in Graves' disease", J Immunol. 181(6):4397-405 (2008).
Ugradar, S, et al., "Teprotumumab for non-inflammatory thyroid eye disease (TED): evidence for increased IGF-1R expression", Eye (Lond) 35(9):2607-2612 (2021).
Ugradar, S, et al., "Teprotumumab for the treatment of chronic thyroid eye disease", Eye (Lond) 36(8):1553-1559 (2022).
Varewijck, AJ, et al., "Circulating IgGs may modulate IGF-I receptor stimulating activity in a subset of patients with Graves' ophthalmopathy", J Clin Endocrinol Metab. 98(2):769-76 (2013).
Weightman, DR, et al., "Autoantibodies to IGF-1 binding sites in thyroid associated ophthalmopathy", Autoimmunity 16(4):251-7 (1993).
Wiersinga, W. M. et al., "Clinical assessment of patients with Graves' orbitopathy: the European Group on Graves' Orbitopathy recommendations to generalists, specialists and clinical researchers", European Journal of Endocrinology, 2006, vol. 155, pp. 387-389.
Wiersinga, WM, Nat Clin Pract Endocrinol Metab. 3(5):396-404 (2007).
Zhang, L, et al., "Possible Targets for Nonimmunosuppressive Therapy of Graves' Orbitopathy", J Clin Endocrinol Metab. 99(7):E1183-90 (2014).
Zhao, P, et al., "Insulin-like growth factor 1 promotes the proliferation and adipogenesis of orbital adipose-derived stromal cells in thyroid-associated ophthalmopathy", Exp Eye Res. 107:65-73 (2013).
U.S. Appl. No. 16/256,221; Restriction Response, dated Oct. 16, 2020; 7 pages.
U.S. Appl. No. 16/256,221; Notice of Allowance, dated Aug. 23, 2021; 12 pages.
U.S. Appl. No. 16/293,293; Restriction Requirement, dated Dec. 10, 2020; 5 pages.
U.S. Appl. No. 16/293,293; Notice of Allowance, dated Aug. 20, 2021; 12 pages.
U.S. Appl. No. 17/117,625, Office Action, dated Sep. 14, 2022; 14 pages.
U.S. Appl. No. 17/531,365; Non-Final Office Action, dated Mar. 19, 2024; 18 pages.
Bagtell et al., Pharmacokinetically Guided Phase 1 Trial of the IGF-1 Receptor Antagonist RG1507 in Children with Recurrent or Refractory Solid Tumors. Clin Cancer Res., 17(3):611-9 (2011).
Bartalena et al., Consensus statement of the European Group on Graves' orbitopathy (EUGOGO) on management of GO. Eur J Endocrinol 158(No. 3):273-285 (2008).
Dolman et al., Visa Classification for Graves orbitopathy. Ophthalmic Plast Reconstr Surg 22(No. 5):319-324 (2006).
Dolman., Evaluating Graves' orbitopathy. Best Pract Res Clin Endocrinol Metab 26(No. 3):229-248 (2012).

(56) References Cited

OTHER PUBLICATIONS

Douglas., Teprotumumab, an Insulin-Like Growth Factor-1 Receptor Antagonist Antibody, in the Treatment of Active Thyroid Eye Disease: A Focus on Proptosis. Eye (Lond) 33(2):183-90 (2019).

Gupta., Intention-to-treat concept: A review. Perspect Clin Res. 2(3):109-112 (2011).

Hansson. Aspects of growth factors in exophthalmos. Acta Endocrinologica (Copenh) 121(Suppl. 2):107-11 (1989).

Imai et al., Effect of growth factors on hyaluronan and proteoglycan synthesis by retroocular tissue fibroblasts of Graves' ophthalmopathy in culture. Acta Endocrinol (Copenh). 126(6):541-52 (1992).

Kabat et al. Sequences of Proteins of Immunological Interest. NIH Pub. No. 91-3242. Public Health Service, National Institutes of Health. 1:647-669 (1991).

Kurzrock et al., A Phase I Study of Weekly R1507, A Human Monoclonal Antibody Insulin-like Growth Factor-I Receptor Antagonist, in Patients with Advanced Solid Tumors. Clin Cancer Res., 16(8):2458-65 (2010).

Mourits et al., Clinical activity score as a guide in the management of patients with Graves' ophthalmopathy. Clin Endocrinol (Oxf) 47(No. 1):9-14 (1997).

Mourits et al., Clinical criteria for the assessment of disease activity in Graves' ophthalmopathy: a novel approach. Br J Ophthalmol 73(No. 8):639-644 (1989).

Pappo et al., R1507, a Monoclonal Antibody to the Insulin-Like Growth Factor 1 Receptor, in Patients With Recurrent or Refractory Ewing Sarcoma Family of Tumors: Results of a Phase II Sarcoma Alliance for Research Through Collaboration Study. J Clin Oncol., 29(34):4541-7 (2011).

PCT/US2019/020770 International Preliminary Report on Patentability dated Sep. 17, 2020.

PCT/US2019/020770 International Search Report and Written Opinion dated Jul. 9, 2019.

Piantanida et al., Teprotumumab: A New Avenue for the Management of Moderate-to-Severe and Active Graves' Orbitopathy? J Endocrinol Invest., 40(8):885-7 (2017).

Ramalingam et al., Randomized Phase II Study of Erlotinib in Combination with Placebo or R1507, a Monoclonal Antibody to Insulin-Like Growth Factor-1 Receptor, for Advanced-Stage Non-Small-Cell Lung Cancer. J Clin Oncol., 29(34):4574-80 (2011).

Smith et al., Immunoglobulins from patients with Graves' disease induce hyaluronan synthesis in their orbital fibroblasts through the self-antigen, insulin-like growth factor-I receptor. J Clin Endocrinol Metab. 89(10):5076-80 (2004).

Smith et al., New Advances in Understanding Thyroid-Associated Ophthalmopathy and the Potential Role for nsulin-Like Growth Factor-I Receptor [version 1; referees: 2 approved], F1000 Research 2018, 7(F1000 Faculty Rev):134 Last updated Feb. 1, 2018.

Smith et al., Teprotumumab for Thyroid-Associated Ophthalmopathy. N Engl J Med., 376(18):1748-61 (2017).

U.S. Appl. No. 16/256,221 Office Action dated Apr. 29, 2021.

U.S. Appl. No. 16/293,293 Office Action dated Apr. 29, 2021.

Werner., Classification of the eye changes of Graves' disease. Am J Ophthalmol 68(No. 4):646-648 (1969).

Werner., Modification of the classification of the eye changes of Graves' disease. Am J Ophthalmol 83(No. 5):725-727 (1977).

Xu et al., Comparative Efficacy of Medical Treatments for Thyroid Eye Disease: A Network Meta-Analysis. J Ophthalmol., 2018:7184163 (2018).

U.S. Appl. No. 17/531,365; Final Office Action, dated Jul. 11, 2024; 15 pages.

Xu, N. et al., "Ocular Surface Characteristics and Impression Cytology in Patients with Active versus Inactive Thyroid Eye Disease", Eye Science, vol. 27, No. 2, pp. 64-68 (2012).

U.S. Appl. No. 17/531,365, Notice of Allowance, dated Sep. 13, 2024; 6 pages.

U.S. Appl. No. 18/929,510, Non-Final Office Action, dated Jan. 7, 2025; 15 pages.

METHODS FOR THE TREATMENT OF THYROID EYE DISEASE

This application is a continuation of U.S. application Ser. No. 16/293,293, filed Mar. 5, 2019, which claims the benefit of priority of U.S. Provisional Application No. 62/638,689, filed Mar. 5, 2018, the contents of which are incorporated by reference as if written herein in their entireties.

Thyroid-associated ophthalmopathy (TAO), also known as thyroid eye disease (TED), Graves' ophthalmopathy or orbitopathy (GO), thyrotoxic exophthalmos, dysthyroid ophthalmopathy, and several other terms, is orbitopathy associated with thyroid dysfunction. TAO is divided into two types. Active TAO, which typically lasts 1-3 years, is characterized by an ongoing autoimmune/inflammatory response in the soft tissues of the orbit. Active TAO is responsible for the expansion and remodeling of the ocular soft tissues. The autoimmune/inflammatory response of active TAO spontaneously resolves and the condition transitions into inactive TAO. Inactive TAO is the term used to describe the long-term/permanent sequelae of active TAO.

The cause of TAO is unknown. TAO is typically associated with Graves' hyperthyroidism, but can also occur as part of other autoimmune conditions that affect the thyroid gland and produce pathology in orbital and periorbital tissue, and, rarely, the pretibial skin (pretibial myxedema) or digits (thyroid acropachy). TAO is an autoimmune orbitopathy in which the orbital and periocular soft tissues are primarily affected with secondary effects on the eye and vision. In TAO, as a result of inflammation and expansion of orbital soft tissues, primarily eye muscles and adipose, the eyes are forced forward (bulge) out of their sockets—a phenomenon termed proptosis or exophthalmos.

The annual incidence rate of TAO has been estimated at 16 cases per 100,000 women and 2.9 cases per 100,000 men from a study based in one largely rural Minnesota community. There appears to be a female preponderance in which women are affected 2.5-6 times more frequently than men; however, severe cases occur more often in men than in women. In addition, most patients are aged 30-50 years, with severe cases appearing to be more frequent in those older than 50 years. Although most cases of TAO do not result in loss of vision, this condition can cause vision-threatening exposure keratopathy, troublesome diplopia (double vision), and compressive dysthyroid optic neuropathy.

TAO may precede, coincide with, or follow the systemic complications of dysthyroidism. The ocular manifestations of TAO include upper eyelid retraction, lid lag, swelling, redness (erythema), conjunctivitis, and bulging eyes (exophthalmos or proptosis), chemosis, periorbital edema, and altered ocular motility with significant functional, social, and cosmetic consequences.

Many of the signs and symptoms of TAO, including proptosis and ocular congestion, result from expansion of the orbital adipose tissue and periocular muscles. The adipose tissue volume increases owing in part to new fat cell development (adipogenesis) within the orbital fat. The accumulation of hydrophilic glycosaminoglycans, primarily hyaluronic acid, within the orbital adipose tissue and the perimysial connective tissue between the extraocular muscle fibers, further expands the fat compartments and enlarges the extraocular muscle bodies. Hyaluronic acid is produced by fibroblasts residing within the orbital fat and extraocular muscles, and its synthesis in vitro is stimulated by several cytokines and growth factors, including IL-1β, interferon-γ, platelet-derived growth factor, thyroid stimulating hormone (TSH) and insulin-like growth factor I (IGF-I).

TAO is commonly considered to be the autoimmune orbital manifestation of Graves' Disease (GD). However, only approximately 30% of patients with Graves' hyperthyroidism manifest clinically relevant ocular pathology indicating there is mechanistic heterogeneity and differentiation between the conditions. The molecular mechanisms underlying TAO remain unclear. It is accepted that the generation of autoantibodies that act as agonists on the thyroid-stimulating hormone receptor (TSHR) is responsible for Graves' hyperthyroidism. Pathogenic overstimulation of TSHR, leads to overproduction of thyroid hormones (T3 and T4) and accelerated metabolism of many tissues.

In active TAO, autoantibodies trigger connective tissue and fat to expand, in part from stimulating excessive synthesis of hyaluronan. The expanded tissues are infiltrated with T and B cells, become inflamed, and get and extensively remodeled. It has been suggested that TSHR might have some pathogenic role in the development of active TAO. Indeed, a positive correlation has been found between anti-TSHR antibodies and the degree of TAO activity. However, no definitive link has been established, and a proportion of TAO patients remain euthyroid throughout the course of their disease.

Antibodies that activate the insulin-like growth factor I receptor (IGF-IR) have also been detected and implicated in active TAO. Without being bound to any theory, it is believed that TSHR and IGF-IR form a physical and functional complex in orbital fibroblasts, and that blocking IGF-IR appears to attenuate both IGF-1 and TSH-dependent signaling. It has been suggested that blocking IGF-IR using an antibody antagonist might reduce both TSHR- and IGF-I-dependent signaling and therefore interrupt the pathological activities of autoantibodies acting as agonists on either receptor.

IGF-IR is a widely expressed heterotetrameric protein involved in the regulation of proliferation and metabolic function of many cell types. It is a tyrosine kinase receptor comprising two subunits. IGF-IRα contains a ligand-binding domain while IGF-IRβ is involved in signaling and contains tyrosine phosphorylation sites. Monoclonal antibodies directed against IGF-IR have been developed and assessed as a therapeutic strategy for several types of solid tumors and lymphomas.

Management of hyperthyroidism due to Graves' disease is imperfect because therapies targeting the specific underlying pathogenic autoimmune mechanisms of the disease are lacking. Even more complex is the treatment of moderate-to-severe active TAO. Although recent years have witnessed a better understanding of its pathogenesis, TAO remains a therapeutic challenge and dilemma. There are no approved drugs to treat active TAO. Intravenous glucocorticoids (ivGCs) and oral glucocorticoids are used to treat patients with moderate-to-severe active TAO, but results are seldom satisfactory. Partial responses are frequent and relapses (rebound) after drug withdrawal are not uncommon. Adverse events do occur and many patients eventually require rehabilitative surgery conducted when their condition has transitioned to inactive TAO.

Recently, attention has been focused on the use of biologicals, which might specifically intervene on the pathogenic mechanisms of TAO. In 2015 two small, monocenter, randomized clinical trials (RCTs) investigated the effects of rituximab, a CD20+ B cell-depleting agent, versus placebo or ivGCs, respectively. The results from the two trials were conflicting; they were negative (no differences with placebo) in the first trial, but positive (beneficial effects comparable to ivGCs) in the second one. The effectiveness of rituximab for moderate-to-severe active TAO therefore remains to be determined. The recent guidelines published by the European Thyroid Association/European Group on Graves' Orbitopathy (EUGOGO) indicate rituximab as a possible second-line treatment for patients poorly responsive to a first course of ivGCs. As with rituximab, there is no dependable evidence concerning other potential therapeutic agents, such as adalimumab, etanercept, infliximab, or monoclonals or small molecules blocking the TSH receptor. The use of the interleukin-6 receptor monoclonal antibody, tocilizumab, based on an ongoing RCT also remains to be determined.

As stated above, medical therapies for moderate-to-severe TAO that have proved to be effective and safe in adequately powered, prospective, placebo-controlled trials are lacking. Previous clinical trials, which were rarely placebo-controlled, suggest that high dose glucocorticoids, alone, or with radiotherapy, can reduce inflammation-related signs and symptoms in patients with active ophthalmopathy, but only minimally affect proptosis and can cause dose-limiting adverse reactions.

Immunoglobulins that activate IGF-IR signaling have been detected in patients with GD and TAO. Furthermore, IGF-I synergistically enhances the actions of thyrotropin. IGF-IR, a membrane-spanning tyrosine kinase receptor with roles in development and metabolism, also stimulates immune function and thus might be targeted therapeutically in autoimmune diseases. IGF-IR is overexpressed by orbital fibroblasts and by T cells and B cells in persons with GD and TAO. It forms a signaling complex with TSHR through which it is transactivated. In vitro studies of orbital fibroblasts and fibrocytes show that IGF-IR-inhibitory antibodies can attenuate the actions of IGF-I, thyrotropin, thyroid-stimulating immunoglobulins, and immunoglobulins isolated from patients with GD and TAO.

These observations prompted a trial of teprotumumab, a fully human IGF-IR-inhibitory monoclonal antibody, in patients with active, moderate-to-severe TAO. Although this trial of teprotumumab proved successful and reduced proptosis by at least 2 mm and reduced the clinical activity score (CAS) by at least 2 points in several patients, there were some patients who either did not respond to this treatment or, responded to the treatment and later relapsed.

DETAILED DESCRIPTION

Provided herein are antibodies against insulin-like growth factor I receptor (IGF-IR) for use in the treatment of GO or TAO.

Also provided herein is a method of reducing proptosis in an eye in a subject with thyroid-associated ophthalmopathy (TAO), thyroid eye disease (TED) or Graves' ophthalmopathy (GO) who has previously undergone prior treatment with an antibody, or an antigen binding fragment thereof, that specifically binds to and/or inhibits insulin like growth factor-I receptor (IGF-IR) and either did not respond to said prior treatment or responded to said prior treatment and later relapsed, comprising administering to said subject an effective amount of the antibody, or an antigen binding fragment thereof, wherein said antibody specifically binds to and inhibits insulin like growth factor-I receptor (IGF-IR).

Also provided herein is a method of reducing proptosis by at least 2 mm in an eye without a deterioration of 2 mm or more in the other (or fellow eye) in a subject with TAO comprising administering to said subject an effective amount of an antibody, or an antigen binding fragment thereof, wherein said antibody specifically binds to and inhibits Insulin Like Growth Factor-I Receptor (IGF IR). The subject is one who has undergone prior treatment with said antibody or antigen binding fragment thereof, and either did not respond to said prior treatment or relapsed after said prior treatment.

In some embodiments, the reduction in proptosis or exophthalmos could be greater than 2 mm, for example, 2.2 mm, 2.4 mm, 2.5 mm, 2.6 mm. 2.8 mm, 3 mm, 3.2 mm, 3.4 mm, 3.5 mm, 3.6 mm, 3.8 mm, 4 mm, 4.1 mm, 4.2 mm, 4.3 mm, 4.4 mm, 4.5 mm, 4.6 mm, 4.7 mm, 4.8 mm, 4.9 mm, 5 mm or more than 5 mm.

Also provided herein is a method of reducing Clinical Activity Score (CAS) of thyroid-associated ophthalmopathy (TAO) in a subject who has undergone prior treatment with an antibody, or an antigen binding fragment thereof, that specifically binds to and inhibits IGF-IR, and either did not respond to said prior treatment or relapsed after said prior treatment, comprising administering to a subject in need thereof an effective amount of an antibody, or an antigen binding fragment thereof, wherein said antibody specifically binds to and inhibits IGF-IR.

In some embodiments, CAS is reduced in said subject to either one (1) or zero (0) (on the 7-point version of the CAS scale—as described below).

In some embodiments, the reduction in CAS is by 2 points or more, for example, by 3, 4, 5, 6, or 7 points. In one embodiment, the reduction in CAS is by 2 or more points. In another embodiment, it is by 3 or more points. In yet another embodiment, the reduction in CAS is by 4 or more points. In yet another embodiment, the reduction in CAS is by 5 or more points.

In one embodiment, as a result of the treatment, the CAS is reduced to one (1). In another embodiment, as a result of the treatment, the CAS is reduced to zero (0).

Also provided herein is a method of reducing the severity of, or treating, thyroid-associated ophthalmopathy (TAO) comprising administering to a subject who has undergone prior treatment with an antibody, or an antigen binding fragment thereof, that specifically binds to and inhibits IGF-IR, and either did not respond to said prior treatment or responded to said prior treatment and later relapsed, the antibody, or an antigen binding fragment thereof, wherein said antibody specifically binds to and inhibits IGF-IR. The antibody may be administered in the following amounts: about 10 mg/kg antibody as a first dose; and about 20 mg/kg antibody in subsequent doses.

Also provided herein is a method of treating or reducing the severity of thyroid-associated ophthalmopathy (TAO) in a subject who has undergone prior treatment with an antibody, or an antigen binding fragment thereof, that specifically binds to and/or inhibits insulin like growth factor-I receptor (IGF-IR) and either did not respond to said prior treatment or relapsed after said prior treatment comprising administering to a subject in need thereof an effective amount of an antibody, or an antigen binding fragment thereof, wherein said antibody specifically binds to and inhibits IGF-IR, and wherein said antibody (i) reduces proptosis by at least 2 mm in an eye; (ii) is not accompanied by a deterioration of 2 mm or more in the other (or fellow eye); and (iii) reduces the CAS in said subject to either one (1) or zero (0) (on the 7-point version of the scale—as described below.

Also provided herein is a method of treating or reducing the severity of TAO (TED or GO) comprising administering to a subject in need thereof an effective amount of an antibody, or an antigen binding fragment thereof, wherein said antibody specifically binds to and inhibits IGF-IR, and wherein said antibody reduces proptosis by at least 2 mm as well as reduces the CAS to either one (1) or zero (0). As stated above, the subject is one who has undergone prior treatment with said antibody or antigen binding fragment thereof, and either did not respond to said prior treatment or relapsed after said prior treatment.

Also provided herein is a method of treating or reducing the severity of TAO (TED or GO) in a subject with TAO who has previously undergone prior treatment with an antibody, or an antigen binding fragment thereof, that specifically binds to and/or inhibits insulin like growth factor-I receptor (IGF-IR) and either did not respond to said prior treatment or responded to said prior treatment and later relapsed, comprising administering to a subject in need thereof an effective amount of a pharmaceutical composition comprising an antibody that specifically binds to and inhibits IGF-IR, or an antigen binding fragment thereof, and a pharmaceutically acceptable excipient or diluent or carrier.

Also provided herein is a method of reducing proptosis in an eye in a subject with TAO who has previously undergone prior treatment with an antibody, or an antigen binding fragment thereof, that specifically binds to and/or inhibits insulin like growth factor-I receptor (IGF-IR) and either did not respond to said prior treatment or responded to said prior treatment and later relapsed, comprising administering to said subject an effective amount of the antibody, or an antigen binding fragment thereof, wherein said antibody specifically binds to and inhibits insulin like growth factor-I receptor (IGF-IR).

Also provided herein is a method of treating or reducing the severity of thyroid-associated ophthalmopathy (TAO) comprising administering to a subject who has undergone prior treatment with an antibody, or an antigen binding fragment thereof, that specifically binds to and inhibits IGF-IR, and either did not respond to said prior treatment or responded to said prior treatment and later relapsed, the antibody, or an antigen binding fragment thereof, wherein said antibody specifically binds to and inhibits IGF-IR.

Also provided herein is a method of improving the quality of life in a subject with thyroid-associated ophthalmopathy (TAO, also called Graves' Ophthalmopathy/Graves' Orbitopathy) who has undergone prior treatment with an antibody, or an antigen binding fragment thereof, that specifically binds to and inhibits IGF-IR, and either did not respond to said prior treatment or responded to said prior treatment and later relapsed, comprising administering to the subject an effective amount of an antibody, or an antigen binding fragment thereof, wherein the antibody specifically binds to and inhibits IGF-IR.

Also provided herein is a method of treating or reducing diplopia or the severity of diplopia in a subject with thyroid-associated ophthalmopathy (TAO) who has undergone prior treatment with an antibody, or an antigen binding fragment thereof, that specifically binds to and inhibits IGF-IR, and either did not respond to said prior treatment or responded to said prior treatment and later relapsed, comprising administering to the subject an effective amount of an antibody, or an antigen binding fragment thereof, wherein the antibody specifically binds to and inhibits IGF-IR.

In some embodiments, the diplopia is constant diplopia. In some embodiments, the diplopia is inconstant diplopia. In some embodiments, the diplopia is intermittent diplopia.

In some embodiments, the improvement in or reduction in severity of diplopia is sustained at least 20, 30, 40, or 50 weeks after discontinuation of antibody administration. In some embodiments, the improvement in or reduction in severity of diplopia is sustained 20-30, 30-40, 40-50, or 50-60 weeks after discontinuation of antibody administration. In some embodiments, the improvement in or reduction in severity of diplopia is sustained at least 20 weeks after discontinuation of antibody administration. In some embodiments, the improvement in or reduction in severity of diplopia is sustained at least 50 weeks after discontinuation of antibody administration.

Also provided herein is a method of treating or reducing the severity of constant diplopia (CD) in a subject with thyroid-associated ophthalmopathy (TAO) who has undergone prior treatment with an antibody, or an antigen binding fragment thereof, that specifically binds to and inhibits IGF-IR, and either did not respond to said prior treatment or responded to said prior treatment and later relapsed, comprising administering to the subject an effective amount of an antibody, or an antigen binding fragment thereof, wherein the antibody specifically binds to and inhibits IGF-IR (e.g., teprotumumab). In some embodiments, the treatment with teprotumumab improves the CD QoL in patients with severe TAO.

Also provided herein is a method of treating or reducing the severity of diplopia in a subject with thyroid-associated ophthalmopathy (TAO) who has undergone prior treatment with an antibody, or an antigen binding fragment thereof, that specifically binds to and inhibits IGF-IR, and either did not respond to said prior treatment or responded to said prior treatment and later relapsed, comprising administering to the subject an effective amount of an antibody, or an antigen binding fragment thereof, wherein the antibody specifically binds to and inhibits IGF-IR (e.g., teprotumumab), that results in improved diplopia relative to placebo which is sustained out to 51 weeks after drug discontinuation.

In some embodiments, the antibody, or an antigen binding fragment thereof, comprises the complementarity determining regions or heavy and/or light chain variable regions as disclosed herein. In some embodiments, the antibody, or an antigen binding fragment thereof, that is administered to the subject comprises: (i) heavy chain complementarity determining region (CDR) 1, 2 and 3, .i.e., CDR1, CDR2, and CDR3 amino acid sequences and light chain CDR1, CDR2, and CDR3 amino acid sequences as set forth in SEQ ID NOs: 1-6, respectively; or (ii) heavy chain CDR1, CDR2, and CDR3 amino acid sequences and light chain CDR1, CDR2, and CDR3 amino acid sequences as set forth in SEQ ID NOs: 1, 9, 3, 4, 10, 6, respectively. In some embodiments, the antibody, or an antigen binding fragment thereof, that is administered to the subject comprises the heavy chain CDRs and the light chain CDRs of teprotumumab.

In some embodiments, the antibody, or an antigen binding fragment thereof, that is administered to the subject comprises: (i) a heavy chain variable region comprising the amino acid sequence of SEQ ID NO: 7 and a light chain variable region comprising the amino acid sequence of SEQ ID NO: 8; or (ii) a heavy chain variable region comprising the amino acid sequence of SEQ ID NO: 11 and a light chain variable region comprising the amino acid sequence of SEQ ID NO: 12. In some embodiments, the antibody, or an antigen binding fragment thereof, that is administered to the subject comprises the heavy chain variable region and light chain variable region of teprotumumab.

In some embodiments, the antibody that is administered to the subject is antibody 1 or antibody 2, as disclosed herein, or an antigen binding fragment thereof. In some embodiments, antibody 1 is teprotumumab.

When administered to a population of patients, about 20%, 25%, 30%, 35%, 40%, 45%, 50%, 55%, 60%, 65%, 70%, 75%, 80%, 85%, 90%, 95% or 100% of the patients may respond with a reduction in proptosis or exophthalmos by at least 2 mm, a reduction in the CAS of at least 2 points, an improvement in quality of life as measured by the GO-QoL or either the functioning or appearance subscale thereof or any individual measure thereof, a reduction in diplopia or the severity of diplopia or constant diplopia, or any combination of the foregoing measures. In some embodiments, the response is seen in at least 20%, or at least 25%, or at least 30%, or at least 35%, or at least 40%, or at least 45%, or at least 50%, or at least 55%, or at least 60%, or at least 65%, or at least 70%, or at least 80% of the patients.

In some embodiments, the antibody, or an antigen binding fragment thereof, reduces proptosis by at least 3 mm in at least 25%, 30%, 35%, 40%, 45% 50%, 55%, 60%, 65%, 70%, 75%, 80%, or 85% of the subjects. In some embodiments, the antibody, or an antigen binding fragment thereof, reduces proptosis by at least 3.5 mm in at least 25%, 30%, 35%, 40%, 45% 50%, 55%, 60%, 65%, 70%, 75%, 80%, or 85% of the subjects. In some embodiments, the antibody, or an antigen binding fragment thereof, reduces proptosis by at least 4 mm in at least 25%, 30%, 35%, 40%, 45% 50%, 55%, 60%, 65%, 70%, 75%, 80%, or 85% of the subjects. In some embodiments, the antibody, or an antigen binding fragment thereof, reduces proptosis by at least 4 mm in about 40% of the subjects.

The antibody, or an antigen binding fragment thereof, can be administered in a single dose or in multiple doses. In one embodiment, the therapeutic antibody is administered to the subject in a single dose. In another embodiment, the therapeutic antibody is administered to the subject in multiple doses, spread out over the course of a few days, weeks or months. In some embodiments the antibody, or an antigen binding fragment thereof, is administered every week or every 2 weeks or every 3 weeks or every 4 weeks or every 5 weeks or every 6 weeks or every 7 weeks or every 8 weeks or every month or every 2 months or every 3 months.

In some embodiments the antibody, or an antigen binding fragment thereof, is administered in multiple doses and the dosage is the same each time. In some embodiments the antibody, or an antigen binding fragment thereof, is administered in multiple doses and the dosage at the time of first administration is different (could be higher or lower) from those at subsequent times. In some embodiments the antibody, or an antigen binding fragment thereof, is administered in multiple doses and the dosage is adjusted at each administration based on the subject's response to the therapy.

The dosage may further vary between patients, based on different factors such as the age, gender, race, and body weight of each patient. In one embodiment, the dosage varies by body weight of the patient. The dosage could range from about 1 mg of the antibody, or an antigen binding fragment thereof, per kilogram of body weight to about 100 mg of the antibody, or an antigen binding fragment thereof, per kilogram of body weight. The dosage, could for example, be 1 mg, 2 mg, 3 mg, 5 mg, 7 mg, 10 mg, 12 mg, 15 mg, 17 mg, 20 mg, 22 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg, of the antibody, or an antigen binding fragment thereof, per kilogram of body weight.

In some embodiments, the dosage is about 1 mg/kg to about 5 mg/kg of the antibody, or an antigen binding fragment thereof. In some embodiments, the dosage is about 5 mg/kg to about 10 mg/kg of the antibody, or an antigen binding fragment thereof. In some embodiments, the dosage is about 10 mg/kg to about 15 mg/kg of the antibody, or an antigen binding fragment thereof. In some embodiments, the dosage is about 15 mg/kg to about 20 mg/kg of the antibody, or an antigen binding fragment thereof.

In some embodiments where the antibody, or an antigen binding fragment thereof, is administered in multiple doses and the dosage at the time of first administration is different from those at subsequent times, the dosage at the time of first administration is about 1 mg/kg to about 5 mg/kg of the antibody, or an antigen binding fragment thereof; or about 5 mg/kg to about 10 mg/kg of the antibody, or an antigen binding fragment thereof; or about 10 mg/kg to about 15 mg/kg of the antibody, or an antigen binding fragment thereof; or about 15 mg/kg to about 20 mg/kg of the antibody, or an antigen binding fragment thereof; or about 20 mg/kg to about 25 mg/kg of the antibody, or an antigen binding fragment thereof. The subsequent dose(s) could be higher or lower than the first dose. In some embodiments, the subsequent dose is about 1 mg/kg to about 5 mg/kg of the antibody, or an antigen binding fragment thereof; or about 5 mg/kg to about 10 mg/kg of the antibody, or an antigen binding fragment thereof; or about 10 mg/kg to about 15 mg/kg of the antibody, or an antigen binding fragment thereof; or about 15 mg/kg to about 20 mg/kg of the antibody, or an antigen binding fragment thereof; or about 20 mg/kg to about 25 mg/kg of the antibody, or an antigen binding fragment thereof.

The duration of the treatment would depend on the subject's response to the therapy and can range from about one month or 4 weeks to about 2 years or 100 weeks. In different embodiments, the treatment may be provided over a total duration of about 1 month, 2 months, 3 months, 4 months, 5 months, 6 months, 7 months, 8 months, 9 months, 10 months, 11 months, 1 year, 14 months, 16 months, 18 months, 20 months, 22 months or 2 years. In other embodiments, the treatment may be provided over a total duration of 4, 6, 8, 10, 12, 14, 16, 20, 22, 24, 26, 28, 30, 32, 34, 36, 38, 40, 42, 44, 46, 48, 50, 52 weeks, or extended to 56, 64, 72, 80, 88, 96 or 104 weeks.

In one embodiment, the antibody, or an antigen binding fragment thereof, is administered for a duration of 24 weeks at intervals of 3 weeks starting with an initial dose of 10 mg per kilogram of body weight, followed by 20 mg per kilogram for seven additional infusions.

The antibody, or an antigen binding fragment thereof, may be administered by any suitable route including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer pharmaceutical compositions. Typically, the therapeutic antibody may be prepared as a freeze-dried (lyophilized) powder or as an injectable, either as a liquid solution or suspension. Solid forms suitable for solution in, or suspension in, liquid vehicles prior to injection may also be used.

Provided herein are the following specific embodiments.

Embodiment 1. A method of treating or reducing the severity of, thyroid-associated ophthalmopathy (TAO), or a symptom thereof, comprising administering to a subject who has undergone prior treatment with an antibody, or an antigen binding fragment thereof, that specifically binds to and inhibits IGF-IR, and either did not respond to said prior treatment or responded to said prior treatment and later relapsed, the antibody, or an antigen binding fragment thereof, wherein said antibody specifically binds to and inhibits IGF-IR.

Embodiment 2. A method of reducing proptosis in an eye in a subject with thyroid-associated ophthalmopathy (TAO) who has previously undergone prior treatment with an antibody, or an antigen binding fragment thereof, that specifically binds to and/or inhibits insulin like growth factor-I receptor (IGF-IR) and either did not respond to said prior treatment or responded to said prior treatment and later relapsed, comprising administering to said subject an effective amount of the antibody, or an antigen binding fragment thereof, wherein said antibody specifically binds to and inhibits insulin like growth factor-I receptor (IGF-IR).

Embodiment 3. A method of reducing Clinical Activity Score (CAS) of thyroid-associated ophthalmopathy (TAO) in a subject who has undergone prior treatment with an antibody, or an antigen binding fragment thereof, that specifically binds to and inhibits IGF-IR, and either did not respond to said prior treatment or relapsed after said prior treatment, comprising administering to a subject in need thereof an effective amount of an antibody, or an antigen binding fragment thereof, wherein said antibody specifically binds to and inhibits IGF-IR.

Embodiment 4. A method of a) reducing proptosis by at least 2 mm and b) reducing the clinical activity score (CAS) in a subject with thyroid-associated ophthalmopathy (TAO) who has previously undergone prior treatment with an antibody, or an antigen binding fragment thereof, that specifically binds to and/or inhibits insulin like growth factor-I receptor (IGF-IR) and either did not respond to said prior treatment or responded to said prior treatment and later relapsed, comprising administering to the subject an effective amount of an antibody, or an antigen binding fragment thereof, wherein the antibody specifically binds to and inhibits insulin like growth factor-I receptor (IGF-IR).

Embodiment 5. The method of any of Embodiments 1, 2, and 4, wherein proptosis is reduced by at least 2 mm.

Embodiment 6. The method of Embodiment 5, wherein proptosis is reduced by at least 3 mm.

Embodiment 7. The method of Embodiment 5, wherein proptosis is reduced by at least 4 mm.

Embodiment 8. The method of any of Embodiments 1, 3, and 4, wherein the clinical activity score (CAS) of the subject is reduced by at least 2 points.

Embodiment 9. The method of Embodiment 8, wherein the clinical activity score (CAS) of the subject is reduced to one (1).

Embodiment 10. The method of Embodiment 9, wherein the clinical activity score (CAS) of the subject is reduced to zero (0).

Embodiment 11. A method of treating or reducing the severity of thyroid-associated ophthalmopathy (TAO) in a subject who has undergone prior treatment with an antibody, or an antigen binding fragment thereof, that specifically binds to and/or inhibits insulin like growth factor-I receptor (IGF-IR) and either did not respond to said prior treatment or relapsed after said prior treatment comprising administering to a subject in need thereof an effective amount of an antibody, or an antigen binding fragment thereof, wherein said antibody specifically binds to and inhibits IGF-IR, and wherein treatment with said antibody (i) reduces proptosis by at least 2 mm in an eye; (ii) is not accompanied by a deterioration of 2 mm or more in the other (or fellow eye); and (iii) reduces the CAS in said subject to either one (1) or zero (0).

Embodiment 12. A method of improving the quality of life in a subject with thyroid-associated ophthalmopathy (TAO, also called Graves' Ophthalmopathy/Graves' Orbitopathy) who has undergone prior treatment with an antibody, or an antigen binding fragment thereof, that specifically binds to and inhibits IGF-IR, and either did not respond to said prior treatment or responded to said prior treatment and later relapsed, comprising administering to the subject an effective amount of an antibody, or an antigen binding fragment thereof, wherein the antibody specifically binds to and inhibits IGF-IR.

Embodiment 13. The method of Embodiment 12, wherein the quality of life is measured by the Graves' Ophthalmopathy Quality of Life (GO-QoL) assessment, or either the Visual Functioning or Appearance subscale thereof.

Embodiment 14. The method of Embodiment 13, wherein the treatment results in an improvement of ≥8 points on the GO-QoL.

Embodiment 15. The method of Embodiment 14, wherein the treatment results in an improvement on the Functioning subscale of the GO-QoL.

Embodiment 16. The method of Embodiment 14, wherein the treatment results in an improvement on the Appearance subscale of the GO-QoL.

Embodiment 17. A method of treating or reducing the severity of diplopia in a subject with thyroid-associated ophthalmopathy (TAO) who has undergone prior treatment with an antibody, or an antigen binding fragment thereof, that specifically binds to and inhibits IGF-IR, and either did not respond to said prior treatment or responded to said prior treatment and later relapsed, comprising administering to the subject an effective amount of an antibody, or an antigen binding fragment thereof, wherein the antibody specifically binds to and inhibits IGF-IR.

Embodiment 18. The method of Embodiment 17, wherein the diplopia is constant diplopia.

Embodiment 19. The method of Embodiment 17, wherein the diplopia is inconstant diplopia.

Embodiment 20. The method of Embodiment 17, wherein the diplopia is intermittent diplopia.

Embodiment 21. The method of Embodiment 17, wherein the improvement in or reduction in severity of diplopia is sustained at least 20 weeks after discontinuation of antibody administration.

Embodiment 22. The method of Embodiment 17, wherein the improvement in or reduction in severity of diplopia is sustained at least 50 weeks after discontinuation of antibody administration.

Embodiment 23. The method of any one of Embodiments 1-22, wherein said antibody is administered at a dosage of about 1 mg/kg to about 5 mg/kg antibody as a first dose.

Embodiment 24. The method of any one of Embodiments 1-22, wherein said antibody is administered at a dosage of about 5 mg/kg to about 10 mg/kg antibody as a first dose.

Embodiment 25. The method of any one of Embodiments 1-22, wherein said antibody is administered at a dosage of about 5 mg/kg to about 20 mg/kg antibody in subsequent doses.

Embodiment 26. The method of any one of Embodiments 1-22, wherein said antibody is administered in the following amounts: about 10 mg/kg antibody as a first dose; and about 20 mg/kg antibody in subsequent doses.

Embodiment 27. The method of Embodiment 26, wherein said subsequent doses are administered every three weeks for at least 21 weeks.

Embodiment 28. The method of any one of Embodiments 1-27, wherein the antibody, or an antigen binding fragment thereof, comprises a heavy chain comprising CDR1, CDR2 and CDR3 and a light chain comprising CDR1, CDR2 and CDR3, wherein the heavy chain CDR1, CDR2, and CDR3 amino acid sequences and light chain CDR1, CDR2, and CDR3 amino acid sequences are at least 90% identical to (i) the amino acid sequences of SEQ ID NOs: 1-6, respectively; or (ii) the amino acid sequences of SEQ ID NOs: 1, 9, 3, 4, 10, 6, respectively.

Embodiment 29. The method of any one of Embodiments 1-27, wherein the antibody, or an antigen binding fragment thereof, comprises: (i) heavy chain CDR1, CDR2, and CDR3 amino acid sequences and light chain CDR1, CDR2, and CDR3 amino acid sequences as set forth in SEQ ID NOs: 1-6, respectively; or (ii) heavy chain CDR1, CDR2, and CDR3 amino acid sequences and light chain CDR1, CDR2, and CDR3 amino acid sequences as set forth in SEQ ID NOs: 1, 9, 3, 4, 10, 6, respectively.

Embodiment 30. The method of Embodiment 28 or 29, wherein the antibody, or an antigen binding fragment thereof, comprises: (i) a heavy chain variable region having at least 80% sequence identity to the amino acid sequence of SEQ ID NO: 7 and a light chain variable region having at least 80% sequence identity to the amino acid sequence of SEQ ID NO: 8; or (ii) a heavy chain variable region having at least 80% sequence identity to the amino acid sequence of SEQ ID NO: 11 and a light chain variable region having at least 80% sequence identity to the amino acid sequence of SEQ ID NO: 12.

Embodiment 31. The method of Embodiment 30, wherein the antibody, or an antigen binding fragment thereof, comprises: (i) a heavy chain variable region comprising the amino acid sequence of SEQ ID NO: 7 and a light chain variable region comprising the amino acid sequence of SEQ ID NO: 8; or (ii) a heavy chain variable region comprising the amino acid sequence of SEQ ID NO: 11 and a light chain variable region comprising the amino acid sequence of SEQ ID NO: 12.

Embodiment 32. The method of any one of Embodiments 1-28, wherein the antibody is antibody 1 or antibody 2, or an antigen binding fragment thereof.

Embodiment 33. The method of any one of Embodiments 1-28, wherein the antibody, or an antigen binding fragment thereof, is a human antibody, a monoclonal antibody, a human monoclonal antibody, a purified antibody, a diabody, a single-chain antibody, a multi-specific antibody, Fab, Fab', F(ab')2, Fv or scFv.

Embodiment 34. The method of any one of Embodiments 1-28, wherein the antibody, or an antigen binding fragment thereof, is administered in a pharmaceutical composition that additionally comprises a pharmaceutically acceptable diluent or excipient or carrier.

Embodiment 35. The method of Embodiment 34, wherein the pharmaceutical composition further comprises one or more pharmaceutically active compounds for the treatment of TAO.

Embodiment 36. The method of Embodiment 34 or 35, wherein the pharmaceutical composition further comprises corticosteroids; rituximab or other anti-CD20 antibodies; tocilizumab or other anti-IL-6 antibodies; or selenium, infliximab or other anti-TNFα antibodies or a thyroid-stimulating hormone receptor (TSHR) inhibitor.

Embodiment 37. A method of treating or reducing the severity of thyroid-associated ophthalmopathy (TAO) comprising administering to a subject who has undergone prior treatment with an antibody, or an antigen binding fragment thereof, that specifically binds to and inhibits IGF-IR, and either did not respond to said prior treatment or responded to said prior treatment and later relapsed, the antibody, or an antigen binding fragment thereof, wherein said antibody specifically binds to and inhibits IGF-IR, wherein the antibody is administered in the following amounts:

about 10 mg/kg antibody as a first dose; and
about 20 mg/kg antibody in subsequent doses.

Embodiment 38. The method of Embodiment 37, wherein said subsequent doses are administered every three weeks for at least 21 weeks.

Embodiment 39. The method of Embodiment 38, wherein the antibody is teprotumumab, or an antigen binding fragment thereof.

Embodiment 40. The method of Embodiment 39, wherein the antibody or antigen binding fragment thereof is administered by injection.

Also provided are embodiments wherein any embodiment above may be combined with any one or more of these embodiments, provided the combination is not mutually exclusive. As used herein, two embodiments are "mutually exclusive" when one is defined to be something which is different than the other.

The following terms shall be understood to have the meanings ascribed herein.

As used herein, "Thyroid-associated Ophthalmopathy" (TAO), "Thyroid Eye Disease" (TED), "Graves' Ophthalmopathy" or "Graves' Orbitopathy" (GO) refer to the same disorder or condition and are used interchangeably. They all refer to the inflammatory orbital pathology associated with some autoimmune thyroid disorders, most commonly with "Graves' Disease" (GD), but sometimes with other diseases, e.g. Hashimoto's thyroiditis.

The terms "proptosis" and "exophthalmos" (also known as exophthalmus, exophthalmia, or exorbitism) refer to the forward projection, displacement, bulging, or protrusion of an organ. As used herein, the terms refer to the forward projection, displacement, bulging, or protrusion of the eye anteriorly out of the orbit. Proptosis and exophthalmos are considered by some of skill in the art to have the same meaning and are often used interchangeably, while others attribute subtle differences to their meanings. Exophthalmos is used by some to refer to severe proptosis; or to refer to endocrine-related proptosis. Yet others use the term exophthalmos when describing proptosis associated with the eye, in, for example, subjects with TAO (TED or GO).

As used herein, the terms "proptosis" and "exophthalmos" are used interchangeably and refer to the forward projection, displacement, bulging, or protrusion of the eye anteriorly out of the orbit. Owing to the rigid bony structure of the orbit with only anterior opening for expansion, any increase in orbital soft tissue contents taking place from the side or from behind will displace the eyeball forward. Proptosis or exophthalmos can be the result of a several disease processes including infections, inflammations, tumors, trauma, metastases, endocrine lesions, vascular diseases & extra orbital lesions. TAO (TED or GO) is currently recognized as the most common cause of proptosis in adults. Exophthalmos can be either bilateral, as is often seen in TAO (TED or GO), or unilateral (as is often seen in an orbital tumor).

Measurement of the degree of exophthalmos can be performed using an exophthalmometer, an instrument used for measuring the degree of forward displacement of the eye. The device allows measurement of the forward distance of the lateral orbital rim to the front of the cornea.

Computed tomography (CT) scanning and Magnetic resonance imaging (MRI) may also be used in evaluating the degree of exophthalmos or proptosis. CT scanning is an excellent imaging modality for the diagnosis of TAO. In addition to allowing visualization of the enlarged extraocular muscles, CT scans provide the surgeon or clinician with depictions of the bony anatomy of the orbit when an orbital decompression is required. MRI, with its multi-planar and inherent contrast capabilities, provides excellent imaging of the orbital contents without the radiation exposure associated with CT scan studies. MRI provides better imaging of the optic nerve, orbital fat, and extraocular muscle, but CT scans provide better views of the bony architecture of the orbit.

Orbital ultrasonography can also be a used for the diagnosis and evaluation of TAO, because it can be performed quickly and with a high degree of confidence. High reflectivity and enlargement of the extraocular muscles are assessed easily, and serial ultrasonographic examinations can also be used to assess progression or stability of the ophthalmopathy.

Based on the technologies currently available, or that will become available in the future, one of skill in the art would be capable of determining the best modality for diagnosing and evaluating the extent of proptosis or exophthalmos.

Although it is generally accepted that the normal range of proptosis is 12-21 mm, it must be noted that the value for a normal person varies by age, gender and race. For example, in normal adult white males, the average distance of globe protrusion is 16.5 mm, with the upper limit of normal at 21.7 mm. In adult African Americans it averages 18.2 mm, with an upper normal limit of 24.1 mm in males and 22.7 mm in females. In Mexican adults, males averaged 15.2 mm and females averaged 14.8 mm and in Iran, for the age group of 20-70 years, the average was 14.7 mm. In Taiwanese adults, comparing normal subjects to those with Graves Ophthalmopathy, the normal group had an average reading of 13.9 mm versus 18.3 mm for the TAO group.

Even within a group of people, there can be variability. Four ethnic groups in Southern Thailand had exophthalmometry measurement averages ranging from 15.4 mm to 16.6 mm. In 2477 Turkish patients, the median measurement was 13 mm, with an upper limit of 17 mm; and in a Dutch study, the upper limit was 20 mm in males and 16 mm in females.

Although the average and upper limits for exophthalmos or proptosis vary widely, it is accepted in the field that a difference greater than 2 mm between the eyes is significant and not normal.

One of skill in the art, for example an ophthalmologist, surgeon or other clinician skilled in the knowledge and treatment of eye disorders would know what a normal value of proptosis is based on the age, gender and race of the subject and have the ability to diagnose or evaluate the presence or absence of proptosis as well as track its progression.

Activity Measures and Assessments

Several classification systems have been conceived to assess the clinical manifestations of TAO. In 1969, Werner reported the NOSPECS Classification (No physical signs or symptoms, Only signs, Soft tissue involvement, Proptosis, Extraocular muscle signs, Corneal involvement, and Sight loss) (Werner, S. C. *American Journal of Ophthalmology*, 1969, 68, no. 4, 646-648.)

The modified NOSPECS was also published by Werner in 1977 and has been broadly used since then (Werner, S. C. *American Journal of Ophthalmology*, 1977, 83, no. 5, 725-727). This classification grades for clinical severity and does not provide a means of distinguishing active TAO (inflammatory progressive) from inactive TAO (noninflammatory stationary). Therefore, the indication for treatments used to be based exclusively in the severity of symptoms without consideration whether the disease was active or inactive. In 1989, Mourits et al. described the Clinical Activity Score (CAS) (Mourits et al., *British Journal of Ophthalmology*, 1989, 73, no. 8, 639-644) as a way of assessing the degree of active disease. This score, based on the classical signs of acute inflammation (pain, redness, swelling, and impaired function) was proposed as a clinical classification to discriminate easily between active and inactive disease and was modified in 1997 (Mourits et al., *Clinical Endocrinology*, 1997. 47, no. 1, 9-14). This protocol is further described in Table 1 below.

As used herein, the term Clinical Activity Score (CAS) refers to the protocol described and scored according to Table 1. According to this protocol, one point is given for the presence of each of the parameters assessed in the Table below. The sum of all points defines clinical activity and provides the CAS, where 0 or 1 constitutes inactive disease and 7 severe active ophthalmopathy.

As provided in Table 1, the CAS consists of seven components: spontaneous retrobulbar pain, pain on attempted eye movements (upward, side-to-side, and downward gazes), conjunctival redness, redness of the eyelids, chemosis, swelling of the caruncle/plica, and swelling of the eyelids. Each component is scored as present (1 point) or absent (0 points). The score at each efficacy assessment is the sum of all items present; giving a range of 0-7, where 0 or 1 constitutes inactive disease and 7 severe active ophthalmopathy. A change of >2 points is considered clinically meaningful.

TABLE 1

Parameters for calculating Clinical Activity Score (CAS).

| Item. No. | Parameter |
|---|---|
| 1 | spontaneous retrobulbar pain |
| 2 | pain on attempted eye movements (upward, side-to-side, and downward gazes; sometimes termed gaze evoked orbital pain) |
| 3 | Eyelid swelling |
| 4 | Eyelid erythema (redness) |
| 5 | Conjunctival redness |
| 6 | Chemosis (swelling/edema of the conjunctiva) |
| 7 | Swelling of caruncle or plica |

Item 1, spontaneous orbital pain could be a painful, or oppressive feeling on, or behind, the globe. This pain may be caused by the rise in intraorbital pressure, when the orbital tissues volume increases through excess synthesis of extracellular matrix, fluid accumulation, and cellular infiltration and expansion. Item 2, gaze evoked orbital pain, could be pain in the eyes when looking, or attempting to look, up, down or sideways, i.e., pain with upward, downward, or lateral eye movement, or when attempting eye movement. This kind of pain could arise from the stretching of the inflamed muscle(s), especially on attempted upgaze. The 'stretching pain' cannot be provoked by digital pressing on the eyeball, as would be expected if it were a manifestation of the raised intraorbital pressure. Both kinds of pain can be reduced after anti-inflammatory treatment. These kinds of pain are therefore considered to be directly related to autoimmune inflammation in the orbit and thus useful in assessing TAO activity.

Swelling in TAO is seen as chemosis (edema of the conjunctiva), item no. 6 in Table 1, and swelling of the caruncle and/or plica semilunaris. Both are signs of TAO activity. Swollen eyelids can be caused by edema, fat prolapse through the orbital septum, or fibrotic degeneration.

In addition to swelling, other symptoms indicative of active TAO include redness and/or pain of the conjunctiva, eyelid, caruncle and/or plica semilunaris.

Other grading systems have also been developed for the assessment of GO. The VISA Classification (vision, inflammation, strabismus, and appearance) (Dolman, P. J., and Rootman, J., *Ophthalmic Plastic and Reconstructive Surgery*, 2006, 22, no. 5, 319-324 and Dolman, P. J., *Best Practice & Research Clinical Endocrinology & Metabolism*, 2012, 26, no. 3, 229-248) and the European Group of Graves' Orbitopathy (EUGOGO) Classification (Bartalena, L., et al., *European Journal of Endocrinology*, 2008, 158, no. 3, 273-285) are two such examples. Both systems are grounded in the NO SPECS and CAS classifications and use indicators to assess the signs of activity and the degree of severity. More importantly, they allow the clinician to guide the treatment of the patient with GO. VISA is more commonly used in North America and Canada while EUGOGO is in Europe. Since the VISA and EUGOGO protocols are not interchangeable, only one of them should be employed as a reference in a specific patient.

Severity Measures

For lid aperture, the distance between the lid margins are measured (in mm) with the patient looking in the primary position, sitting relaxed, and with distant fixation.
For swelling of the eyelids, the measure/evaluation is either "absent/equivocal," "moderate," or "severe."
  Redness of the eyelids is either absent or present.
  Redness of the conjunctivae is either absent or present.
  Conjunctival edema is either absent or present.
  Inflammation of the caruncle or plica is either absent or present.
  Exophthalmos is measured in millimeter using the same Hertel exophthalmometer and same intercanthal distance for an individual patient.
  Subjective diplopia is scored from 0 to 3 (0=no diplopia; 1=intermittent, i.e., diplopia in primary position of gaze, when tired or when first awakening; 2=inconstant, i.e., diplopia at extremes of gaze; 3=constant, i.e., continuous diplopia in primary or reading position).
  For eye muscle involvement, the ductions are measured in degrees.
  Corneal involvement is either absent/punctate or keratopathy/ulcer.
  For optic nerve involvement, .i.e., best-corrected visual acuity, color vision, optic disc, relative afferent pupillary defect, the condition is either absent or present. In addition, visual fields are checked if optic nerve compression is suspected.

Severity Classification

Sight-threatening thyroid eye disease: Patients with dysthyroid optic neuropathy (DON) and/or corneal breakdown. This category warrants immediate intervention.

Moderate-to-severe thyroid eye disease: Patients without sight-threatening disease whose eye disease have sufficient impact on daily life to justify the risks of immunosuppression (if active) or surgical intervention (if inactive). Patients with moderate-to-severe thyroid eye disease usually have any one or more of the following: lid retraction ≥2 mm, moderate or severe soft tissue involvement, exophthalmos ≥3 mm above normal for race and gender, inconstant or constant diplopia.

Mild thyroid eye disease: Patients whose features of thyroid eye disease have only a minor impact on daily life insufficient to justify immunosuppressive or surgical treatment. They usually have only one or more of the following: minor lid retraction (<2 mm), mild soft tissue involvement, exophthalmos <3 mm above normal for race and gender, transient or no diplopia, and corneal exposure responsive to lubricants.

Graves Ophthalmopathy Quality of Life (GO-QoL)

In addition to proptosis (or exophthalmos) and CAS, quality of life is also evaluated with the use of the GO quality of life (GO-QoL) questionnaire. This questionnaire is designed to determine the improved quality of life after treatment with a method disclosed herein. In some embodiments, questionnaire may determine the decreased or lack of side effects after being treated with an antibody, or an antigen binding fragment thereof, according to a method disclosed herein as compared to treatment with glucocorticoids.

As described below in Example 18, the GO-QoL is a 16-item self-administered questionnaire divided into 2 subsets and used to assess the perceived effects of TED by the subjects on (i) their daily physical activity as it relates to visual function, and (ii) psychosocial functioning.

The questionnaire has two self-assessment subscales. Each subscale has 8 questions which are answered with: (i) yes—very much so; (ii) yes—a little; or (iii) no—not at all. Each question is scored 0-2, respectively, and the total raw score is then mathematically transformed to a 0-100 scale, where 0 represents the most negative impact on quality of life, and 100 represents no impact. A change of >8 points on the 0-100 scale is considered to be clinically meaningful. The combined score takes raw scores from both subscales and again transforms them to a single 0-100 scale.

Assessment of Gorman Grading of Diplopia

The Gorman assessment of subjective diplopia includes four categories: no diplopia (absent), diplopia when the patient is tired or awakening (intermittent), diplopia at extremes of gaze (inconstant), and continuous diplopia in the primary or reading position (constant). Patients are scored according to which grade of diplopia they are experiencing. An improvement of ≥1 grade is considered clinically meaningful.

To facilitate understanding of the disclosure, a number of terms and abbreviations as used herein are defined below as follows:

As used herein, the term "antibody" encompasses the various forms of antibodies including but not being limited to whole antibodies, monoclonal antibodies, antibody fragments, human antibodies, humanized antibodies, chimeric antibodies and genetically engineered antibodies as long as the characteristic properties such as specificity and IGF-IR inhibitory are retained.

As used herein, the terms "antigen binding fragment," "fragment," and "antibody fragment" are used interchangeably to refer to any fragment that comprises a portion of a full length antibody, generally at least the antigen binding portion or the variable region thereof. Examples of antibody fragments include, but are not limited to, diabodies, single-chain antibody molecules, multispecific antibodies, Fab, Fab', F(ab')$_2$, Fv or scFv. Further, the term "antibody" as used herein includes both antibodies and antigen binding fragments thereof. In addition, antibody fragments comprise single chain polypeptides having the characteristics of a VH chain, namely being able to assemble together with a VL chain or of a VL chain binding to IGF-IR, namely being able to assemble together with a VH chain to a functional antigen binding pocket and thereby providing the property of inhibiting the binding of IGF-I and IGF-II to IGF-IR.

The terms "monoclonal antibody" or "monoclonal antibody composition," as used herein refer to a preparation of antibody molecules of a single amino acid composition. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light human chain transgene fused to an immortalized cell.

The term "human antibody" as used herein, is intended to include antibodies having variable and constant regions derived from human germline immunoglobulin sequences. The term "humanized antibody" as used herein refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody."

The term "recombinant human antibody," as used herein, is intended to include all human antibodies that are prepared, expressed, created or isolated by recombinant means, such as antibodies isolated from a host cell such as an SP2-0, NS0 or CHO cell or from an animal (e.g., a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form.

The term "variable region" (variable region of a light chain (VL), variable region of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play an important role in the binding specificity/affinity of antibodies.

The terms "complementarity determining region," "CDR," "hypervariable region," or "antigen-binding portion of an antibody" are used interchangeably herein and refer to the amino acid residues of an antibody which are responsible for antigen-binding. The hypervariable region comprises amino acid residues from the complementarity determining regions or CDRs. "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. Especially, CDR3 of the heavy chain is the region which contributes most to antigen binding. CDR and FR regions are determined according to the standard definition of Kabat et al., Sequences of Proteins of Immunological Interest, 5th Ed. Public Health Service, National Institutes of Health, Bethesda, MD. (1991)) and/or those residues from a "hypervariable loop."

The terms "binding to IGF-IR" or "specific binding to IGF-IR" are used interchangeably herein and mean the binding of the antibody to IGF-IR in an in vitro assay, preferably in a binding assay in which the antibody is bound to a surface and binding of IGF-IR is measured by Surface Plasmon Resonance (SPR). Binding means a binding affinity ($K_D$) of $10^{-8}$ M or less, preferably $10^{-13}$ to $10^{-9}$ M. Binding to IGF-IR can be investigated by a BIAcore assay (Pharmacia Biosensor AB, Uppsala, Sweden). The affinity of the binding is defined by the terms ka (rate constant for the association of the antibody from the antibody/antigen complex), kd (dissociation constant), and $K_D$ (kd/ka). The antibodies used in the methods disclosed herein show a $K_D$ of about $10^{-9}$ M or less.

The antibodies, or antigen binding fragments thereof, used in the methods disclosed herein inhibit the binding of IGF-I and IGF-II to IGF-IR. The inhibition is measured as $IC_{50}$ in an assay for binding of IGF-I/IGF-II to IGF-IR on cells. Such an assay is known to one of skill in the art and is described, for example, U.S. Pat. No. 7,579,157, which is incorporated herein in its entirety. The $IC_{50}$ values of the antibodies used in the methods disclosed herein for the binding of IGF-I and IGF-II to IGF-IR are no more than 2 nM. $IC_{50}$ values are measured as average or median values of at least three independent measurements. Single $IC_{50}$ values may be out of the scope.

The term "inhibiting the binding of IGF-I and IGF-II to IGF-IR" as used herein refers to inhibiting the binding of $I^{125}$-labeled IGF-I or IGF-II to IGF-IR presented on the surface of cells in an in vitro assay. Inhibiting means an $IC_{50}$ value of 2 nM or lower.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

The terms "treating," "treatment," and the like, as used herein, mean ameliorating a disease, so as to reduce, ameliorate, or eliminate its cause, its progression, its severity, or one or more of its symptoms, or otherwise beneficially alter the disease in a subject. Reference to "treating," or "treatment" of a patient is intended to include prophylaxis. Treatment may also be preemptive in nature, i.e., it may include prevention of disease in a subject exposed to or at risk for the disease. Prevention of a disease may involve complete protection from disease, for example as in the case of prevention of infection with a pathogen, or may involve prevention of disease progression, for example from prediabetes to diabetes. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The terms "subject" and "patient" are used interchangeably herein to mean all mammals including humans. Examples of subjects include, but are not limited to, humans, monkeys, dogs, cats, horses, cows, goats, sheep, pigs, and rabbits. In one embodiment, the subject or patient is a human.

A subject or patient, as used herein, refers to one who participated in a prior teprotumumab trial or study, and who was either a proptosis non-responder at Week 24 of the prior trial/study, or was a proptosis responder at Week 24 but meet the criteria for re-treatment due to relapse during the follow-up Period of the prior trial/study. This prior trial is described below and, as used herein, the prior teprotumumab trial or study disclosed herein, is referred to as "the prior study," "the prior trial," or "the lead-in study," or "the lead-in trial." The terms "study" and "trial" are used interchangeably herein to refer to a clinical trial.

As used herein, the "study eye" refers to the more severely affected eye on Day1, i.e., the day of the Baseline Visit of a study or trial. The other eye is referred to herein as the non-study eye or the fellow eye. The progress of both eyes may, but need not be, followed as treatment progresses.

The terms "affected with a disease or disorder," "afflicted with a disease or disorder," or "having a disease or disorder" are used interchangeably herein and refer to a subject or patient with any disease, disorder, syndrome or condition. No increased or decreased level of severity of the disorder is implied by the use of one the terms as compared to the other.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

When introducing elements of the present disclosure or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e., A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein in relation to a numerical value x means x±10%.

The term "comprising" encompasses "including" as well as "consisting" e.g., a composition "comprising" X may consist exclusively of X or may include something additional e.g., X+Y.

The word "substantially" does not exclude "completely" e.g., a composition which is "substantially free" from Y may be completely free from Y. Where necessary, the word "substantially" may be omitted.

An "intention-to-treat" population includes all clinical trial subjects who are randomized according to randomized treatment assignment. Randomized controlled trials often suffer from two major complications, i.e., noncompliance and missing outcomes. One potential solution to this problem is a statistical concept called intention-to-treat (ITT) analysis. ITT analysis ignores noncompliance, protocol deviations, withdrawal, and anything that happens after randomization. ITT analysis maintains prognostic balance generated from the original random treatment allocation. In ITT analysis, estimate of treatment effect is generally conservative. A better application of the ITT approach is possible if complete outcome data are available for all randomized subjects. Per-protocol population is defined as a subset of the ITT population who completed the study without any major protocol violations. See, e.g., Gupta S K, Intention-to-treat concept: A review, Perspect Clin Res. 2011 July-September; 2(3): 109-112.

The term "teprotumumab," also known as RV-001 and R-1507, is a human monoclonal antibody that binds to insulin-like growth factor-1 receptor (IGF-1R). It has CAS number 1036734-93-6 and comprises a SEQ ID NOS. 1-8 disclosed herein (see, e.g., table 17). It comprises and may be referred to in the alternative throughout this disclosure as "Antibody 1."

Antibodies

The sequences of the heavy chains and light chains of examples of antibodies that may be used in the methods disclosed herein, each comprising three CDRs on the heavy chain and three CDRs on the light chain are provided below. The sequences of the CDRs, heavy chains, light chains as well as the sequences of the nucleic acid molecules encoding the CDRs, heavy chains and light chains of the antibodies are disclosed in the sequence listing. The CDRs of the antibody heavy chains are referred to as CDRH1 (or HCDR1), CDRH2 (or HCDR2) and CDRH3 (or HCDR3), respectively. Similarly, the CDRs of the antibody light chains are referred to as CDRL1 (or LCDR1), CDRL2 (or LCDR2) and CDRL3 (or LCDR3), respectively. Table 2 provides the SEQ ID numbers for the amino acid sequences of the six CDRs of the heavy and light chains, respectively, of the antibodies that may be used in the methods disclosed herein.

TABLE 2

SEQ ID Numbers for CDR Polypeptides of Antibodies Disclosed Herein.

| | SEQ ID NOs. for CDR Polypeptides | | | | | |
|---|---|---|---|---|---|---|
| | CDRH1 | CDRH2 | CDRH3 | CDRL1 | CDRL2 | CDRL3 |
| Antibody 1 | 1 | 2 | 3 | 4 | 5 | 6 |
| Antibody 2 | 1 | 9 | 3 | 4 | 10 | 6 |

In one embodiment, an antibody or antibody fragment useful in the methods disclosed herein comprises at least one CDR with a sequence that has at least 95% sequence identity to any one of SEQ ID NOs: 1-6, 9, or 10 and specifically inhibits (or blocks) Insulin Like Growth Factor-I Receptor (IGF-IR).

In another embodiment, the antibody or antigen binding fragment that can be used in the methods comprising a heavy chain comprises one or more (i.e. one, two or all three) heavy chain CDRs from antibody 1 or antibody 2 and specifically inhibits or blocks IGF-IR.

In yet another embodiment, the antibody or antigen binding fragment useful in the methods disclosed herein comprises a heavy chain CDR1 with the amino acid sequence of SEQ ID NO: 1; a heavy chain CDR2 with the amino acid sequence of SEQ ID NO: 2, or SEQ ID NO: 9; and a heavy chain CDR3 with the amino acid sequence of SEQ ID NO: 3. In certain embodiments, the antibody or antibody fragment comprises a heavy chain comprising the amino acid sequence of (i) SEQ ID NO: 1 for CDRH1, SEQ ID NO: 2 for CDRH2 and SEQ ID NO: 3 for CDRH3; or (ii) SEQ ID NO: 1 for CDRH1, SEQ ID NO: 9 for CDRH2, and SEQ ID NO: 3 for CDRH3 and specifically inhibits IGF-IR.

In another embodiment, the antibody or antigen binding fragment that can be used in the methods disclosed herein comprising a light chain comprising one or more (i.e. one, two or all three) light chain CDRs from antibody 1 or antibody 2 and specifically inhibits IGF-IR.

In yet another embodiment, an antibody or antibody fragment useful in the methods disclosed herein comprises a light chain CDR1 with the amino acid sequence of SEQ ID NO: 4; a light chain CDR2 with the amino acid sequence of SEQ ID NO: 5, or SEQ ID NO: 10; and a light chain CDR3 with the amino acid sequence of SEQ ID NO: 6. In certain embodiments, the antibody or antibody fragment comprises a light chain comprising the amino acid sequence of (i) SEQ ID NO: 4 for CDRL1, SEQ ID NO: 5 for CDRL2, and SEQ ID NO: 6 for CDRL3; or (ii) SEQ ID NO: 4 for CDRL1, SEQ ID NO: 10 for CDRL2, and SEQ ID NO: 6 for CDRL3.

In one embodiment, the antibody, or antigen binding fragment thereof, comprises all of the CDRs of antibody 1 as listed in Table 2, and specifically inhibits (or blocks) Insulin Like Growth Factor-I Receptor (IGF-IR). In another embodiment, an antibody, or antigen binding fragment thereof, comprises all of the CDRs of antibody 2 as listed in Table 2, and specifically inhibits (or blocks) IGF-IR.

The SEQ ID numbers for the amino acid sequence for the heavy chain variable region (VH) and the light chain variable region (VL) of antibodies useful in the methods disclosed herein are listed in Table 3.

TABLE 3

SEQ ID Numbers for $V_H$ and $V_L$ amino acid for Antibodies Disclosed Herein.

| | $V_H$ amino acid | $V_L$ amino acid |
|---|---|---|
| Antibody 1 | 7 | 8 |
| Antibody 2 | 11 | 12 |

In one embodiment, the antibody or antigen binding fragment that can be used in the methods disclosed herein comprises a heavy chain variable region having an amino acid sequence that is about 70%, 75%, 80%, 85%, 90%, 95%, 97%, 98%, 99% or 100% identical to the sequence recited in SEQ ID NOs: 7 or 11 wherein the antibody specifically inhibits IGF-IR.

In another embodiment, the antibody or antigen binding fragment that can be used in the methods disclosed herein specifically inhibits IGF-IR and comprises a heavy chain variable region comprising the amino acid sequence of SEQ ID NO: 7 and a light chain variable region comprising the amino acid sequence of SEQ ID NO: 8; or a heavy chain variable region comprising the amino acid sequence of SEQ ID NO: 11 and a light chain variable region comprising the amino acid sequence of SEQ ID NO: 12.

Examples of antibodies useful in the methods disclosed herein include, but are not limited to, antibody 1, and antibody 2. In some embodiments, antibody 1 is teprotumumab.

Variant antibodies are also included within the scope of the disclosure. Thus, variants of the sequences recited in the application are also included within the scope of the disclosure. Such variants include natural variants generated by somatic mutation in vivo during the immune response or in vitro upon culture of immortalized B cell clones. Alternatively, variants may arise due to the degeneracy of the genetic code or may be produced due to errors in transcription or translation.

Further variants of the antibody sequences having improved affinity and/or potency may be obtained using methods known in the art and are included within the scope of the disclosure. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences disclosed herein are also within the scope of the disclosure.

In one embodiment variant antibody sequences may share 70% or more (i.e. 75%, 80%, 85%, 90%, 95%, 97%, 98%, 99% or more) amino acid sequence identity with the sequences recited in the application. In some embodiments such sequence identity is calculated with regard to the full length of the reference sequence (i.e. the sequence recited in the application). In some further embodiments, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Antibodies used with the methods disclosed herein can be coupled to a drug for delivery to a treatment site or coupled to a detectable label to facilitate imaging of a site comprising cells of interest. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody and an epitope of interest can be facilitated by attaching a detectable substance to the antibody and detecting the antibody-antigen complex by suitable detection means known to one of skill in the art.

Antibodies, or antigen binding fragments thereof, used with the methods disclosed herein can be of any isotype (e.g., IgA, IgG, IgM i.e. an α, γ or μ heavy chain). In one embodiment the antibody is IgG. Within the IgG isotype, antibodies may be IgG1, IgG2, IgG3 or IgG4 subclass. The antibodies may have a κ or a λ light chain.

The antibodies, or an antigen binding fragments thereof, used with the methods disclosed herein can be administered by any route known to one of skill in the art. Non-exhaustive examples of routes that can be used are provided below.

Pharmaceutical Compositions

The pharmaceutical compositions used in the methods disclosed herein comprise one or more of: the antibodies or antibody fragments described above and a pharmaceutically acceptable carrier or excipient. Although the carrier or excipient may facilitate administration, it should not itself induce the production of antibodies harmful to the subject or individual receiving the composition; nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles, and are known to one of skill in the art.

The antibodies, or an antigen binding fragments thereof, or pharmaceutical compositions used with the methods disclosed herein may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions disclosed herein. Typically, the therapeutic compositions may be prepared as injectables, either as liquid solutions or suspensions. Solid forms suitable for solution in, or suspension in, liquid vehicles prior to injection may also be prepared.

In one embodiment, the antibody, or an antigen binding fragment thereof, or pharmaceutical composition is administered intravenously. In another embodiment, the antibody, or an antigen binding fragment thereof, or pharmaceutical composition is administered by intravenous infusion.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g., whether a pharmaceutical should be delivered daily, weekly, monthly, etc. Frequency and dosage may also depend on the severity of symptoms.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

The methods of the present invention can use an antibody, or an antigen binding fragment thereof, as described above, alone or in combination with other pharmaceutically active compounds, to treat conditions such as those disclosed hereinabove. The additional pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of an antibody, or an antigen binding fragment thereof, of the present invention and one or more additional pharmaceutically active compounds.

In some embodiments, the antibody, or an antigen binding fragment thereof, of the present invention is used in combination with existing therapies, including, but not limited to, corticosteroids; rituximab and other anti-CD20 antibodies; tocilizumab and other anti-IL-6 antibodies; or selenium, infliximab and other anti-TNFα antibodies. In some embodiments, the antibody, or an antigen binding fragment thereof, of the present invention is used in combination with TSHR inhibitors.

EXAMPLES

Exemplary embodiments of the present invention are provided in the following Examples which, though written in past tense, may not yet have been performed. The following examples are presented only by way of illustration and to assist one of ordinary skill in using the invention. The examples are not intended in any way to otherwise limit the scope of the invention.

Prior or Lead-In Trial

A multicenter, double-masked, randomized, placebo-controlled clinical trial was conducted to determine the efficacy and safety of teprotumumab in patients with active, moderate-to-severe TAO. A total of 88 patients were randomly assigned to receive placebo or active drug administered intravenously once every 3 weeks for a total of eight infusions. Patients received eight intravenous infusions, starting with an initial dose of 10 mg per kilogram of body weight, followed by 20 mg per kilogram once every 3 weeks for the remaining seven infusions.

The randomized trial was designed to assess efficacy and safety. Patients were randomly assigned in the double-masked intervention phase to either of two intervention groups in a 1:1 ratio in blocks of two, stratified within each clinical center according to smoking status with the use of an interactive Web-response system. Study pharmacists who were aware of the trial-group assignments prepared the masked infusion. The on-site principal investigators could identify a patient's intervention (teprotumumab or placebo) only in the case of an emergency.

The primary end point was the response in the study eye (selected by investigators at baseline as the more affected eye). This response was defined as a reduction of 2 points or more in the Clinical Activity Score (CAS) and a reduction of 2 mm or more in proptosis at week 24. CAS scores could ranging from 0 to 7, with a score of ≥4 indicating moderate to severe active TAO. Secondary end points, measured as continuous variables, included proptosis, the CAS, and results on the Graves' ophthalmopathy-specific quality-of-life questionnaire. Adverse events were also assessed.

The trial was conducted at 15 sites. Major inclusion criteria were the following: patients were 18 to 75 years of age, with TAO that were enrolled into the study no more than 9 months after the onset of orbital symptoms, had a Clinical Activity Score of 4 or more on a 7-point scale in the more severely affected (study) eye, and had not received surgical or medical treatment, with the exception of oral glucocorticoids (a cumulative dose of ≤1 g of methylprednisolone or equivalent, with a 6-week washout period). Serum glucose levels in patients with diabetes were well controlled. Female patients had negative pregnancy tests and used approved contraception. Patients with optic neuropathy, severe ocular surface damage, or an improved CAS of 2 points or more between screening and baseline visits were excluded.

The trial comprised three phases: screening (2 to 6 weeks), intervention (24 weeks), and follow-up (48 weeks). Screening involved one to three visits. During the intervention phase, patients were assessed at baseline and every 3 weeks for 24 weeks; efficacy was assessed at weeks 6, 12, 18, and 24. Data from week 24 were used to assess the primary and secondary end points. With the exception of rare instances, at every assessment, patients were evaluated by the same ophthalmologist, who was unaware of the trial-group assignments. A change of 2 points in the 7-component CAS was considered to be clinically relevant. Proptosis was assessed with the use of a Hertel exophthalmometer. Quality of life was evaluated with the use of the Graves' ophthalmopathy-specific quality-of-life questionnaire (GO-QOL), comprising two subscales assessed separately or in combination; scores on each subscale as well as the score on the overall GO-QOL scale had a range of 0 to 100 points. A change of 8 points was considered to be clinically relevant. Subjective diplopia was assessed by categorizing patients according to four grades. A change of one grade was considered to be clinically relevant.

The results of the study were published in Smith T J et al., "Teprotumumab for Thyroid-Associated Ophthalmopathy," N Engl J Med 2017, 376;18, 1748-61. See also, Study No. NCT01868997 on ClinicalTrials.gov.

Example 1. Description of Clinical Trial to Determine the Efficacy and Safety of Teprotumumab (Antibody 1)

A multi-center, open-label extension study of the study described above as the prior or lead-in trial is being conducted at study centers in the United States and Europe to examine the safety and efficacy of teprotumumab in the treatment of TED in adult subjects. Subjects who completed the 24-week double-masked Treatment Period in the lead-in trial and were proptosis non-responders or were proptosis responders at Week 24 but meet the criteria for re-treatment due to relapse during the follow-up period of the lead-in trial/study are eligible for enrollment. The study treatment previously administered in the lead-in trial/study (teprotumumab or placebo) remained masked throughout this extension study.

All subjects who choose to participate receive up to 8 infusions of teprotumumab (10 mg/kg for the first infusion followed by 20 mg/kg for the remaining 7 infusions) in an open-label fashion, with the number of infusions determined by the investigator's clinical judgment (but not to exceed 8 infusions). The Baseline (Day 1) visit of this extension study occurs within 14 days after the final visit of the lead-in study (Week 24 for proptosis non-responders and up to Week 72 for subjects who relapsed). During the open-label Treatment Period, study drug infusions are scheduled for Day 1 (Baseline), and Weeks 3, 6, 9, 12, 15, 18, and 21 (with a final visit at Week 24 of the 24-Week Treatment Period).

All study drug dosing is performed at the clinic under the supervision of clinic staff, and at any scheduled infusion, the infusion rate may be reduced or the dose may be interrupted or held based on decreased tolerability (as described in examples below). On each dosing day, scheduled assessments (except for adverse event (AE) and concomitant medication use monitoring, which is monitored throughout the clinic visit) are completed prior to study drug dosing. After each of the first 2 infusions, subjects are contacted by phone/email the following day and returned to the clinic 1 week after the infusion (Weeks 1 and 4) for safety and tolerability assessments; additional phone/email contacts and clinic visits are also conducted for any subject experiencing an infusion-associated event.

After completion of the Treatment Period, subjects who are proptosis non-responders in the lead-in trial enter a 24-week Follow-Up Period, during which study drug is not administered and clinic visits are scheduled for 1, 3, and 6 months (Visits Month 7, 9 and 12) after Week 24; subjects discontinued from the Follow-Up Period prior to the Month 12 Visit, return to the clinic and undergo the scheduled Month 12 assessments prior to study discharge. Those who complete the Month 12 Visit will be contacted 6 and 12 months later via phone or email by research staff to enquire if any treatment for TED has been received since last study contact. If yes, subject will be questioned regarding type of treatment and outcome/response. Subjects who relapsed during the follow-up period of the lead-in trial and choose to enter this extension study do not participate in the Follow-Up Period. For these subjects, the last clinic visit is at Week 24. Those who complete the Week 24 Visit will be contacted 6 and 12 months later via phone or email by research staff to enquire if any treatment for TED has been received since last study contact. If yes, subject will be questioned regarding type of treatment and outcome/response.

The study is monitored by a Data Safety Monitoring Board (DSMB), which advises regarding the continuing safety of study subjects and potential subjects as well as continuing validity and scientific merit of the trial.

Example 2. Study Objectives

The overall objective is to evaluate the safety and efficacy of teprotumumab in the treatment of TED in subjects who participated in the lead-in study and who were either proptosis non-responders at Week 24 of the above mentioned study or were proptosis responders at Week 24 but met the criteria for re-treatment due to relapse during the Follow-Up Period of the above mentioned study.

The primary objective is to evaluate the effect of teprotumumab on the proptosis responder rate (i.e., the percentage of subjects with a ≥2 mm reduction from baseline in the study eye without deterioration [≥2 mm increase] of proptosis in the fellow eye) at Week 24.

Secondary objectives evaluated the effect of teprotumumab on the following:
(1) Percentage of subjects with a Clinical Activity Score (CAS) value of 0 or 1 at Week 24 in the study eye;
(2) Mean change from baseline to Week 24 in proptosis measurement in the study eye;
(3) Diplopia responder rate (i.e., the percentage of subjects with baseline diplopia >0 in study eye who have a reduction of ≥1 grade with no corresponding deterioration [≥1 grade worsening] in the fellow eye) at Week 24; and (4) Mean change from baseline to the Week 24 in the Graves' Ophthalmopathy Quality of Life (GO-QoL) questionnaire overall score.

Exploratory objectives evaluate the effect of teprotumumab on the following:

(1) The overall responder rate (percentage of subjects with ≥2-point reduction in CAS AND ≥2 mm reduction in proptosis from Baseline, provided there is no corresponding deterioration [≥2-point/mm increase] in CAS or proptosis in the fellow eye) at Week 24.

(2) Clinical Measures of Severity individual response status frequencies and percentage of responders for each component of clinical severity at Week 24.

(3) Mean change from Baseline to Week 24 in the CAS.

(4) Overall responder rate at Week 24 stratified by the level of response (high responders, responders, low responders, and non-responders; see Section 9.6.3.2.1 for definitions).

(5) Mean change from Baseline to Week 24 in the GO-QoL questionnaire visual functioning (VF) and appearance (A) subscale scores.

(6) Mean change from Baseline to Week 24 on the motility component of the Clinical Measures of Severity.

(7) Evaluate pharmacokinetic (PK) parameters of teprotumumab to estimate exposure and understand PK-PD relationships.

Example 3. Study Design and Plan

Infusions of Teprotumumab (10 mg/kg on Day 1 followed by 20 mg/kg once every 3 weeks (q3W) for the remaining infusions) are provided to the subjects. The number of infusions is individualized for each subject and is based on the investigator's clinical judgment. The Day 1 Visit occurs within 14 days after the final visit of the prior trial. Visit windows are ±1 day for Weeks 1 and 4, ±3 days for Weeks 3, 6, 9, 12, 15, 18, 21, and 24. The Follow-up period is meant for subjects who were proptosis non-responders in the prior trial only; subjects who relapsed in the prior trial did not participate in the Follow-Up Period. Visit windows during the Follow-up period are ±7 days.

Subjects are contacted by phone/email the day following the first and second infusions for safety and tolerability assessments; phone/email contacts also occur the day after any clinic visit where a subject experiences an infusion-related adverse effect (AE). When the investigator determines that dosing is complete, or if the subject wishes to discontinue dosing, the subject returns to the clinic 3 weeks after the last dose and undergoes the scheduled assessments. Subjects who relapsed in the prior study are discharged from the study after completion of the assessments. If a subject participated in the Follow-Up Period and prematurely discontinued prior to Month 12, he/she returns to the clinic and undergoes the assessments prior to study discharge.

Example 4 provides details regarding the study population. The measurements used in this study for the primary and secondary endpoints (proptosis, CAS, and GO-QoL questionnaire) are established and well-validated endpoints that have been shown to correlate significantly with TED.

This is an open-label extension study. In order to maintain the study mask in the lead-in trial, all subjects in this open-label extension study undergo the same dosing regimen of teprotumumab (10 mg/kg on Day 1 followed by 20 mg/kg q3W for the remaining infusions), regardless if they received teprotumumab or placebo in the prior study.

Given the teratogenic effects of teprotumumab noted in a monkey embryo-fetal development toxicity study in past studies, all subjects (men and women) are required to use adequate contraception and report any pregnancies for at least 6 months after the last dose of study drug. Specifically, female subjects of childbearing potential who are sexually active with a non-vasectomized male partner must agree to use 2 reliable forms of contraception, one of which is recommended to be hormonal, during the trial and for 180 days after the last of study drug. Male subjects who are sexually active with a female partner of childbearing potential must agree to use a barrier contraceptive method from Baseline through 180 days after the last dose of study drug. Six months after the last dose, the estimated plasma concentration (0.2 µg/mL) is considered reasonably safe with a low risk of teratogenicity. Furthermore, a 6-month waiting period is in line with recommendations given for other teratogens, such as cytostatic chemotherapy.

Example 4. Subject Population

Subjects with TED who had completed the 24-week double-masked Treatment Period in the prior trial (Example A) and were proptosis non-responders (<2 mm reduction in proptosis in the study eye) or were proptosis responders at Week 24 in the prior study, but who meet criteria for re-treatment due to relapse during the Follow-Up Period are eligible to enter this open-label extension study. The study population enrolled in the prior trial was well-defined and consistent with the expected target population for whom teprotumumab will be indicated (adult subjects with active moderate-to-severe TED).

The sample size is not based on statistical considerations. Subjects who were proptosis non-responders at Week 24 of the prior trial or who were proptosis responders at Week 24 but meet the criteria for re-treatment due to relapse during the follow-up period of the prior trial are eligible for enrollment.

Example 5. Subject Inclusion Criteria

Eligible subjects must meet/provide all of the following criteria: (1) written informed consent; (2) completed the 24-week double-masked Treatment Period in the lead-in study; (3) proptosis non-responder (<2 mm reduction in proptosis in the study eye) at Week 24 of the lead-in study or proptosis responder at Week 24 who relapsed during the follow-up period of the prior trial; (4) subject is euthyroid with the baseline disease under control, or has mild hypo- or hyperthyroidism (defined as free thyroxine [FT4] and free triiodothyronine [FT3] levels <50% above or below the normal limits) at the most recent clinic visit (and every effort will be made to correct the mild hypo- or hyperthyroidism promptly and to maintain the euthyroid state for the full duration of this clinical trial); (5) alanine aminotransferase (ALT) or aspartate aminotransferase(AST) ≥3 times the upper limit of normal (ULN) or serum creatinine <1.5 times the ULN (according to age) at the most recent clinic visit; (6) diabetic subjects must have well-controlled disease (defined as HgbA1c <9.0% at most recent clinic visit); (7) does not require immediate surgical ophthalmological intervention and is not planning corrective surgery/irradiation during the course of the study; (8) women of childbearing potential must have a negative urine pregnancy test at Baseline/Day 1 and must agree to use 2 reliable forms of contraception during the trial and continue for 180 days after the last dose of study drug (one of the 2 forms of contraception is recommended to be hormonal, such as an oral contraceptive; hormonal contraception is to be in use for at least one full cycle prior to Baseline; highly effective contraceptive methods, when used consistently and correctly, include implants, injectables, combined oral contraceptives, some intrauterine devices (IUDs), sexual abstinence or vasectomized partner; (9) male subjects must be surgically sterile or, if sexually active with a female of childbearing potential, must agree to use a barrier contraceptive method from Baseline through 180 days after the last dose of study drug; (10) subject is willing and able to comply with the prescribed treatment protocol and evaluations for the duration of the study.

Example 6. Subject Exclusion Criteria

Subjects are ineligible if, in the opinion of the investigator, they are unlikely to comply with the study protocol or have a concomitant disease or condition that could interfere with the conduct of the study or potentially put the subject at unacceptable risk. Exclusion criteria from the lead-in trial (excluding screening criteria) also apply to this open-label extension study.

Example 7. Removal of Subjects from Therapy or Assessment

All subjects are free to withdraw from study participation at any time, for any reason, and without prejudice to their further medical care. In addition, the investigator may terminate a subject from the study at any time. The primary reason for discontinuation from the study and/or study drug should be recorded on the electronic case report (eCRF) form using one of the following categories:

Adverse Event (AE). The subject experiences an AE that imposes an unacceptable risk to the subject's health, or the subject is unwilling to continue because of an AE. AEs requiring permanent study drug discontinuation per the protocol include: a drug-related anaphylactic reaction; a persistently severe drug-related AE that does not abate to mild or moderate intensity at least 2 weeks prior to the next scheduled dose; severe drug-related hyperglycemia (e.g., blood glucose >250 mg/dL) that does not abate to mild or moderate intensity with anti-diabetic treatment (dose may be skipped up to 2 times prior to permanently discontinuing study drug; diagnosed or suspected IBD (e.g., diarrhea with or without blood or rectal bleeding associated with abdominal pain or cramping/colic, urgency, tenesmus, or incontinence for more than 4 weeks without a confirmed alternative diagnosis or endoscopic or radiologic evidence of enteritis/colitis without a confirmed alternative diagnosis).

Lack of Efficacy: The Investigator determines that study drug administration is not benefitting the subject, and continued participation poses an unacceptable risk to the subject.

Non-Compliance with Study Drug/Other/Protocol Deviations. The subject has a significant protocol deviation, does not comply with study drug administration schedule, or fails to adhere to other study requirements as stated in the protocol.

Lost to Follow-Up. The subject does not return to the clinic for scheduled assessments, and does not respond to the site's attempts to contact the subject.

Voluntary Withdrawal. The subject wishes to withdraw from the study. The clinical site should attempt to determine the underlying reason for the voluntary withdrawal and document it; if the underlying reason is documented as an AE or lack of efficacy, the category of withdrawal should be marked in the corresponding category and not as voluntary withdrawal.

Study Terminated by Sponsor. The sponsor, IRB, or regulatory agency terminates the study.

Pregnancy.

When treatment is complete, the subjects will undergo the scheduled Week 24 assessments.

Subjects who relapsed during the lead-in study were discharged after completion of the Week 24 assessments.

Subjects who were proptosis non-responders in the lead-in study will participate in the Follow-Up Period. Subjects who enter the Follow-Up Period but prematurely discontinue study participation prior to Month 12 will return for a final visit and undergo the scheduled Month 12 assessments prior to study discharge. Subjects who discontinue due to an AE should be followed until resolution or stabilization of the AE, or an adequate explanation for the event is obtained.

No subject prematurely discontinued from the study for any reason is replaced.

Example 8. Criteria for Responders Who Relapse

If subjects met the response criteria at Week 24 of the prior study but subsequently experience a disease relapse during the 48-week follow-up period of the lead-in/prior study, they will have the option to enter this open-label extension study and receive 8 infusions of teprotumumab. The criteria to determine relapse is the following:

Increase in proptosis of ≥2 mm in the study eye since Week 24 of the prior study, or An increase in CAS of ≥2 points since Week 24 with an absolute CAS of ≥4 in the study eye following Week 24 of the prior study.

In addition to one of the bullet points above, the investigator also considered the subject's symptomology to ensure a relapse had occurred (e.g., new onset of double vision).

Example 9. Dose Regimen and Route of Administration

All study drug dosing is performed at the clinic under the supervision of clinic staff. Subjects receive 8 infusions of teprotumumab (10 mg/kg on Day 1 followed by 20 mg/kg once every 3 weeks (q3W) for the remaining infusions) in an open-label fashion.

The infusion rate may be reduced and the dose may be interrupted or held based on tolerability (as described below). The first and second IV infusions are administered over approximately 90 minutes (but not less than 80 minutes). Subsequent infusions are administered over an approximately 60-minute period (but not less than 50 minutes) providing there are no significant infusion-associated events.

Example 10. Dosage Form, Strength Formulation and Storage

Teprotumumab 500 mg is provided in single-dose 20 mL glass vials as a freeze-dried powder containing, in addition to the drug substance, 20 mmol/L histidine-histidine chloride, 250 mmol/L trehalose, and 0.01% polysorbate 20 (w/w). Prior to administration, each vial containing 500 mg teprotumumab freeze-dried powder is reconstituted with 10 mL of water for injection. The resulting solution has an approximate concentration of 50 mg/mL teprotumumab. Reconstituted teprotumumab solution is further diluted in 0.9% (w/v) sodium chloride (NaCl) solution prior to administration (as described in more detail below).

Doses up to 1800 mg are administered in a total infusion volume of 100 mL, and those above 1800 mg are administered in a total infusion volume of 250 mL. To maintain a constant volume in the infusion bags, a volume equal to the volume of teprotumumab to be placed into the infusion bag is first removed from the infusion bag using a sterile syringe and needle. The appropriate volume of reconstituted drug product solution based on the subject's dose and body weight is withdrawn and the teprotumumab reconstituted drug product solution is diluted with normal saline (0.9% NaCl) in the infusion bag.

Recommended storage conditions for the freeze-dried teprotumumab drug product are between 2° C. to 8° C. (36° F. to 46° F.), protected from light. Storage at ambient temperature of the reconstituted teprotumumab solution is limited to 4 hours.

The IV infusion is administered at room temperature (20° C. to 24° C. [68° F. to 75° F.]). The diluted product is used within 4 hours of preparation. However, if not used within 4 hours, and if dilution has taken place under controlled and validated aseptic conditions, the infusion solution can be stored for up to 24 hours at 2° C. to 8° C. (36° F. to 46° F.). An Investigational Pharmacy Manual will be provided to all sites and further describe these processes in detail.

The volume of study drug to be administered is determined by the Electronic Data Capture (EDC) system and is based on the subject's weight. The first dose is 10 mg/kg, and subsequent doses are 20 mg/kg. Weight is measured on Day 1 and Weeks 12 and 24 during the Treatment Period. The dose on Day 1 may be based on the weight determined at the most recent clinic visit, provided the most recent visit was within the prior 3 weeks. The doses on Week 3 through Week 9 is based on the weight determined on Day 1, the weight used in the Week 12 dose calculation can be the weight determined on Day 1 or the weight obtained at Week 12. The weight obtained at Week 12 can be used to adjust the dose beginning at Week 12 or Week 15 through Week 21, as appropriate.

Example 11. Duration of Treatment and Follow-Up

The duration of the Treatment Period is 24 weeks (6 months), during which 8 infusions of teprotumumab are administered.

Subjects who were proptosis non-responders in the lead-in study are scheduled to participate in a 6-month Follow-Up Period in this extension study; subjects who relapsed in the lead-in study and are retreated in this extension study will not participate in the Follow-Up Period.

Example 12. Dose Modifications, Interruptions, and Delays

Subjects are monitored for immediate infusion-associated events (e.g., nausea, vomiting, facial flushing, warmth, dyspnea, dizziness, hypertension, hypotension, pruritus) and delayed infusion-associated events (e.g., rash). If immediate infusion-associated events are noted, the infusion rate is slowed or interrupted, symptomatic treatment (e.g., antipyretics, antihistamines, beta-agonists, oxygen, IV fluid) is administered, and vital signs (temperature, blood pressure, pulse, and respiratory rate) are monitored every 5 minutes until stable and then every 15 minutes for 2 additional determinations. The infusion may be restarted upon complete resolution of symptoms; however, study drug dosing is permanently discontinued if the event is an anaphylactic reaction.

If delayed infusion-associated events are noted, subjects may continue dosing at the investigator's discretion; however, if a rash worsens following repeated dosing or other signs of serum sickness (e.g., delayed fever, myalgias, arthralgias) are present, study drug dosing is permanently discontinued.

Following the appearance of either immediate or delayed infusion-associated events, subsequent doses may be pre-treated with diphenhydramine (1 to 1.25 mg/kg IV; maximum of 50 mg), ranitidine (50 mg IV), famotidine (0.5 mg/kg IV), dexamethasone (0.4 mg/kg IV; maximum of 20 mg), and/or acetaminophen (500 mg). All subsequent infusions are administered over approximately 90 minutes (but not less than 8-minutes) with vital signs monitored every 15 minutes from the start of the infusion through 60 minutes after infusion completion.

In general, the decision to continue dosing should take into consideration the potential benefit and risk to a subject.

Any severe drug-related AE must revert to mild or moderate in intensity at least 2 weeks prior to the next scheduled dose in order for the dose to be administered; if the AE remains severe in intensity within 2 weeks of the next scheduled dose, the subject will be withdrawn from treatment.

Increase in blood glucose is a known AE observed in previous clinical trials with teprotumumab and other IGF-1R antagonists and is known to respond to treatment. Since a referral for treatment of hyperglycemia may take some time, if the Investigator considered it appropriate to continue the subject in the study, the next scheduled infusion visit may be skipped to allow modified anti-diabetic treatment to show its activity and hyperglycemia to return to mild/moderate level before dosing. The subject is then dosed at the next scheduled visit (i.e., 6 weeks after the previous infusion). Fasting blood glucose levels must return to mild/moderate severity before the next scheduled infusion. The above process of withholding a scheduled infusion is permitted only twice during the study. Any changes to the scheduled dosing interval (q3W) or adjustments in the infusion rate should be reported.

Example 13. Restricted Therapy and Medications

Subjects with a previous orbital irradiation or surgery for TED or who had a planned orbital irradiation or surgery for TED over the course of this study are not eligible for study enrollment. In addition, oral corticosteroids, selenium, biotin, immunosuppressive agents, investigational agents, and illicit drug/alcohol use are restricted as shown in Table 4.

TABLE 4

Restricted Medications and Therapies

| Medication/Therapy | Restricted Dose or Time Period |
| --- | --- |
| Orbital irradiation for TED | Any history or planned procedure during entire study duration (Screening through Week 48 of Follow-Up Period). |
| Eye surgery for TED | Any history or planned procedure during entire study duration (Screening through Week 48 of Follow-Up Period). |
| IV steroid for TED | Any history or planned use during study (IV dexamethasone may be administered for infusion-associated AEs. |
| Oral steriod for TED | Cumulative dose prior to study should not exceed the equivalent of 1 g of methylprednisolone. Oral steroids for TED are not allowed during the entire study duration. |
| IV/oral steroid for conditions other than TED | 3 months prior to Screening of lead-in study through present extension study completion (topical steroids for dermatological conditions and IV dexamethasone for infusion-associated AEs are allowed). |
| Selenium or biotin for TED | 3 weeks prior to Screening of lead-in study through present extension study completion. A multivitamin (taken maximally once daily) containing selenium and/or biotin is allowed. |
| Rituximab (Rituxan ® or MabThera ® ) or tocilizumab (Actemra ® or Roactemra ® ) | Any previous use or anticipated use during the study. |
| Immunosuppressive agent (other than rituximab or tocilizumab) | 3 months prior to Screening of lead-in study through present extension study completion. |
| Investigational agent | 60 days prior to Screening lead-in study through present extension study completion. |
| Illicit drug/alcohol use | History of abuse within the past 2 years or abuse during study. |

Hearing loss and/or ototoxicity is not considered to be an adverse event causally associated with the use of teprotumumab. However, it may be reasonable to avoid ototoxic medications such as systemic administration of aminoglycoside and platinum-based chemotherapy during the study. The following medications may cause muscle spasm/cramps and should be avoided during the study: donepezil, neostigmine, and vincristine.

All concomitant treatment (for TED and other conditions) in the Treatment Period and the Follow-Up Period should be documented.

Example 14. Criteria for Evaluation

Efficacy assessments will be performed for both eyes at each assessment time point. The "study eye" (i.e., the more severely affected eye) will remain the same as that identified at the Baseline (Day 1) Visit of the prior study. Both eyes are assessed for efficacy but the study eye will be used to assess the primary outcome measure.

Efficacy is assessed by proptosis (measured as exophthalmos evaluation of the Clinical Measures of Severity using a Hertel instrument for consistency in measurement), CAS (7-item scale), diplopia (measured as part of the Clinical Measures of Severity) and Clinical Measures of Severity (including motility restriction assessments).

Quality of life is assessed using the GO-QoL questionnaire.

Safety is assessed via AE and concomitant medication use monitoring, immunogenicity testing, physical and ophthalmic examinations, vital signs, clinical safety laboratory evaluations (complete blood count, chemistry (including thyroid panel and HbA1C), and urinalysis), pregnancy testing (if applicable), and electrocardiograms (ECG). The study is also monitored by a Data Safety Monitoring Board (DSMB).

Example 15. Proptosis (Exophthalmos) Assessment

Proptosis assessments is performed using a Hertel exophthalmometer for consistency in measurement, and (except when strictly unavoidable) the same Hertel instrument and same observer is used at each evaluation for the full duration of the study. Additionally, the same intercanthal distance (ICD) is used on each occasion.

Proptosis is measured for each eye on Day 1 and Weeks 6, 12, 18, and 24 (or premature withdrawal [PW]) during the Treatment Period, and at Months 7, 9, and 12 (or PW) during the Follow-Up Period. Measurements are recorded on the Clinical Measures of Severity eCRF under exophthalmos.

Example 16. Clinical Measures of Severity

Based on the EUGOGO Consensus Statement (Bartalena et al, 2008; Wiersinga et al, 2006; see also Mouritis et al., 1989), the CAS is assessed on Day 1 and Weeks 6, 12, 18, and 24 (or PW) during the Treatment Period, and at Months 7, 9, and 12 (or PW) during the Follow-Up Period (see Table 5). Except when strictly unavoidable, the same observer should conduct each evaluation of severity measure for the full duration of the study.

TABLE 5

| Item and Assessment Scale | Minimum change required for classifying overall response |
|---|---|
| Exophthalmos (measured in mm using the same Hertel exophthalmometer provided by the Sponsor for consistency in measurement and same intercanthal distance for each individual patient) | Decrease ≥ 2 mm |
| Lid aperture (distance between the lid margins in mm with the patient looking in the primary position, sitting relaxed and with distant fixation) | Decrease ≥ 2 mm |
| Swelling of the eyelids (absent, mild, moderate, severe) | Decrease ≥ One grade |
| Redness of the eyelids (absent, present) | Decrease ≥ One grade |
| Redness of the conjunctiva (absent, present) | Decrease ≥ One grade |
| Conjunctival edema (absent, present) | Decrease ≥ One grade |
| Inflammation of the caruncle or plica (absent, present) | Decrease ≥ One grade |
| Subjective diplopia score 0 = no diplopia; 1 = intermittent (diplopia in primary position of gaze, when tired or when first awakening); 2 = inconstant (diplopia at extremes of gaze); 3 = constant (continuous diplopia in primary or reading position) | Decrease ≥ One grade |
| Eye muscle involvement (ductions in degrees) | Increase ≥ 8° in at least one direction of gaze |
| Corneal involvement (absent/punctate keratopathy/ulcer) | Decrease ≥ One grade |
| Optic nerve involvement Best corrected visual acuity Color vision Optic disc Relative afferent pupillary defect (APD) (absent/present) Visual fields if optic nerve compression is suspected. | Change of best corrected visual acuity by ≥ 2 lines on Snellen chart, or substantial color vision change, or significant change of visual fields, or significant change in optic disc appearance, or (Dis-) appearance of relative afferent pupillary defect |

Each item (spontaneous orbital pain, gaze evoked orbital pain, eyelid swelling that is considered to be due to active (inflammatory phase) TED/GO, eyelid erythema, conjunctival redness that is considered to be due to active (inflammatory phase) TED/GO (ignore "equivocal" redness), chemosis, and inflammation of caruncle or plica) is scored (1=present; 0=absent) and scores for each item are summed for total score.

Example 17. Motility Restriction—Details for Measurement

Motility is examiner assessed by estimating the degrees of restriction in eye movements. It is assessed at the same time points as the Clinical Measures of Severity described above.

Monocular excursions in horizontal and vertical directions of gaze are recorded using the light reflex (LR) test [Dolman et al, 2012].

The clinician shines a pen light in line with the eye being examined in ambient room light and observes the subject's eye along the light's axis. The subject is asked to look in the 4 cardinal directions and the position of the light reflex is viewed on the surface of the cornea. If the light touches the limbus, the eye is assessed to be turned 45 degrees, if half way between the limbus and pupil edge, the eye is assessed at 30 degrees, and if it is at the pupil edge, it is assessed at 15 degrees. Intermediate ductions are judged by estimating the light position between these points to the nearest 5 degrees.

The monocular ductions of each eye (degrees) are recorded for adduction, abduction, supraduction and infraduction.

Except when strictly unavoidable, the same observer should conduct each duction evaluation for the full duration of the study.

Example 18. Evaluation of Graves' Ophthalmopathy Quality of Life (GO-QoL)

Quality of life is evaluated with the use of the GO QoL questionnaire. The GO-QoL questionnaire [C. B. Terwee et al, 1998] is completed on Day 1 and Weeks 6, 12, and 24 (or PW) during the Treatment Period, and at Months 7 and 12 (or PW) during the Follow-Up Period.

The GO-QoL is a 16-item self-administered questionnaire divided into two self-assessment subscales; one covering impact of visual function on daily activities, the other assesses the impact of self-perceived appearance. The visual function subscale covers activities such as driving, walking outdoors, reading, watching television. The appearance subscale asks the subject questions such as whether ophthalmopathy has altered the subject's appearance, caused other people to have a negative reaction to the subject, caused social isolation, and caused the subject to try to mask his or her appearance. Each subscale has 8 questions which are answered with: yes—very much so; yes—a little; or no—not at all. Each question is scored 0-2, respectively, and the total raw score is then mathematically transformed to a 0-100 scale, where 0 represents the most negative impact on quality of life, and 100 represents no impact. A change of >8 points on the 0-100 scale has been shown to be clinically meaningful. The combined score takes raw scores from both subscales and again transforms them to a single 0-100 scale.

Example 19. Adverse Events

According to ICH, an adverse event (AE) is any untoward medical occurrence in a subject or clinical investigation subject administered a pharmaceutical product and which does not necessarily have a causal relationship with this treatment. An AE can therefore be any unfavorable and unintended sign (including an abnormal laboratory finding), symptom, or disease temporally associated with the use of a medicinal (investigational) product, whether or not considered related to the medicinal (investigational) product.

Pre-existing conditions that worsen during a study are reported as AEs. New findings reported from the on-study ophthalmic examinations are not reported as AEs if, according to the investigator, the abnormalities are related to TED and not considered related to the investigational product.

Unchanged, chronic conditions are not considered AEs and are not recorded on the AE pages of the eCRF unless there is a clear exacerbation of a chronic condition.

Disease progression is considered as a worsening of a subject's condition attributable to the disease for which the study drug is being studied (i.e., TED). It may be an increase in the severity of the disease under study and/or increases in the symptoms of the disease. The development of worsening proptosis may be considered as disease progression and not an AE. Events, which are unequivocally due to disease progression, are reported as AEs if they fulfill any of the SAE criteria or are the reason for discontinuation of treatment with the study drug.

Serious and Non-Serious Adverse Event: A Treatment-emergent adverse event (TEAE), baseline event, or suspected adverse reaction is considered serious if, in the view of either the investigator or sponsor, it results in any of the following outcomes:
  Death. This includes any death that occurs during the conduct of a clinical study, including deaths that appear to be completely unrelated to the study drug (e.g., car accidents).
  Life-threatening adverse experience. An AE or suspected adverse reaction is considered life-threatening if, in the view of either the Investigator or the Sponsor, its occurrence places the subject at immediate risk of death. It does not include an AE or suspected adverse reaction that, had it occurred in a more severe form, might have caused death.
  Persistent or significant disability or incapacity.
  Inpatient hospitalization or prolongation of an existing hospitalization.
  Congenital anomaly or birth defect.
  Other medically important event which, according to appropriate medical judgment, may require medical or surgical intervention to prevent one of the outcomes listed above.

Surgical procedures or other therapeutic interventions themselves are not AEs, but the condition for which the surgery/intervention is required is an AE and is documented accordingly.

Elective surgeries that require hospitalization and treatment received at an emergency room or similar facility are not considered as SAEs unless one of the definitions of an SAE listed above is met.

In addition, hospitalizations for planned procedures are not considered an AE unless they are prolonged hospitalizations, and emergency room visits less than 24 hours in duration are not considered hospitalizations.

A non-serious AE includes any AE that is not described in the previous SAE category.

Unexpected Adverse Event: An AE or suspected adverse reaction is considered unexpected if it is not listed in the Reference Safety Information section of the IB or is not listed with the specificity or severity that has been observed. Unexpected, as used in this definition, also refers to AEs or suspected adverse reactions that are mentioned in the Reference Safety Information as occurring with a class of drugs or as anticipated from the pharmacological properties of the drug, but are not specifically mentioned as occurring with the particular drug under investigation.

Adverse Events of Special Interest: Based on previous clinical experience in TED, the following AESIs are identified for this study:
  Infusion reactions (e.g., nausea, vomiting, facial flushing, warmth, dyspnea, dizziness, hypertension, hypotension, pruritus)
  Hyperglycemia
  Muscle spasms
  Diarrhea.

Documentation of Adverse Events: Adverse events that are ongoing at the completion of the prior study and/or occur prior to dosing on Day 1 of the present study will be considered pre-dose AEs. The TEAE reporting period begins with administration of the first dose of study medication on Day 1 and continues until 3 weeks after the last dose of study drug, and the follow-up AE reporting period begins 3 weeks after the last dose of study drug through completion of the follow-up period (Month 12 or PW). All pre-dose AEs, TEAEs, and AEs during the follow-up period must be recorded in the source documents and in the subject's eCRF.

If the Investigator observes an SAE after study completion that he/she believed was possibly caused by the study medication, the investigator will report this SAE.

Detailed information regarding all SAEs is recorded on the Serious Adverse Event Reporting Form. Whenever possible, the investigator should group together into a single term the signs and symptoms that constitute a single diagnosis. For example, cough, rhinitis, and sneezing might be grouped together as "upper respiratory infection" if the investigator is confident of the diagnosis.

Intensity of Adverse Events: All clinical AEs encountered during the clinical study are reported on the AE form of the CRF. Intensity of AEs are graded on a 5-point scale (mild, moderate, severe, life-threatening, death) and reported in detail on the eCRF.

TABLE 6

Intensity of Adverse Events

| Intensity | Definition | Corresponding NCI Grade |
| --- | --- | --- |
| Mild | discomfort noticed but no disruption of normal daily activity | 1 |
| Moderate | discomfort sufficient to reduce or affect daily activity | 2 |
| Severe | inability to work or perform normal daily activity | 3 |
| Life-Threatening | represents an immediate threat to life | 4 |
| Fatal | results in death | 5 |

Example 20. Relationship of Adverse Event to Study Drug

The relationship of the study drug to each AE is determined by the investigator and the sponsor based on the following definitions:

No reasonable causal relationship (probably not related):
 There is no plausible temporal relationship or there is another explanation that unequivocally provides a more plausible explanation for the event.

Yes, reasonable causal relationship (possibly related):
 There is evidence in favor of a causal relationship (i.e., there is a plausible time course) and at least one of the following criteria apply:
  There is a reasonable pharmacological relationship (or known class effect)
  There is no other more plausible explanation
  There is a positive de-challenge (without active treatment of the event)
  There is a positive re-challenge
  There is a distinguishable dose effect Within the reporting requirement under 21 CFR 312.32 (c)(1)(i), the FDA provides the following examples of types of evidence that would suggest a causal relationship between the drug and the AE.

A single occurrence of an event that is uncommon and known to be strongly associated with drug exposure (e.g., angioedema, hepatic injury, Stevens-Johnson Syndrome).

One or more occurrences of an event that is not commonly associated with drug exposure, but is otherwise uncommon in the population exposed to the drug (e.g., tendon rupture).

An aggregate analysis of specific events observed in a clinical trial (such as known consequences of the underlying disease or condition under investigation or other events that commonly occur in the study population independent of drug therapy) that indicates those events occur more frequently in the drug treatment group than in a concurrent or historical control group.

Example 21. Follow-Up of Adverse Events

Any ongoing study drug-related AE present at the time of study termination, including a clinically significant laboratory test abnormality, is followed until resolved or until the event stabilizes and the overall clinical outcome has been ascertained.

In the event of unexplained, treatment-emergent, clinically significant abnormal laboratory test results or clinically significant changes in laboratory test results, the tests are repeated immediately and followed until the values return to within the reference range or to Baseline for that subject.

Example 22. Medication Error and Overdose

An overdose is defined as a known deliberate or accidental administration of investigational drug, to, or by a study subject, at a dose ≥5% above that which is assigned to that individual subject according to the study protocol.

All cases of medication errors and overdose (with or without associated AEs) are documented on the eCRF in order to capture this important safety information consistently in the database. AEs associated with an overdose and SAEs of overdose are reported. In the event of drug overdose, the subject is treated with symptomatic and supportive care as required.

Example 23. Pregnancy Reporting

Urine pregnancy testing is performed for women of childbearing potential (including those with an onset of menopause <2 years prior to Screening of the lead-in study, non-therapy-induced amenorrhea for <12 months prior to Screening of the lead-in study, or not surgically sterile [absence of ovaries and/or uterus]) at all clinic visits. Urinary pregnancy tests are performed locally.

If a female subject becomes pregnant during the Treatment Period, she should immediately notify the investigator, and teprotumumab dosing should be permanently discontinued. Pregnancy occurring in the partner of a male subject participating in the study should be reported to the investigator and the sponsor. Monitoring of the partner should continue until conclusion of the pregnancy.

Pregnancies occurring up to 180 days after the last dose should also be reported to the Investigator. The investigator should counsel the subject and discuss the possible risks of continuing the pregnancy. If pregnancy continues, monitoring should also be continued to the conclusion of the pregnancy.

Subjects should be instructed to continue contraception for 180 days after their last dose of study drug.

Example 24. Vital Signs

Vital signs (heart rate, blood pressure, respiratory rate, temperature) are measured at all clinic visits. Vital signs are measured pre- and post-infusion on Day 1 and Week 3, and predose on any other infusion day. In addition, if immediate infusion-associated events are noted during the infusion, vital signs are monitored every 5 minutes until stable and then every 15 minutes for 2 additional determinations. Also, vital signs are monitored every 15 minutes from the start of the infusion through 60 minutes after infusion completion for any subsequent infusions after the previous occurrence of immediate or delayed infusion-associated events.

Blood pressure and pulse measurements are obtained with the subject's arm unconstrained by clothing or other material and while the subject is sitting up. When possible, the same arm is used for measurements in all study visits. Temperature is obtained orally or via the ear.

Example 25. Physical and Ophthalmic Examinations, Height, and Weight

A physical examination, including complete undilated ophthalmic examination, is performed at Baseline (Day 1) and thereafter at Weeks 1, 6, 12, 18, and 24 (or PW) during the Treatment Period and Month 12 (or PW) of the follow-up period.

The ophthalmic exam includes best-corrected visual acuity, pupil exam, color vision assessment, Ishihara color plates (or equivalent) or related red desaturation, intraocular pressure and slit lamp exam. If significant abnormalities are noted compared with previous visits, including a loss of 2 lines or more of vision, development of pupil abnormalities including afferent pupillary defect (APD), rise in intraocular pressure, development of corneal infiltrates or other abnormalities not here specified but of concern to the ophthalmologist, further investigations of visual function are conducted according to the ophthalmologist decision.

New findings reported from on-study ophthalmic examinations are not reported as AEs if, according to the investigator, the abnormalities are related to TED and not related to the study drug.

Physical exam includes assessment of presence or absence of pretibial myxedema on Day 1 and Week 24 of the Treatment Period and Month 12/EOS of the follow-up period. If present, measurements of instep and calf are taken.

Weight is measured at Baseline and every 12 weeks throughout the study (Weeks 12 and 24 (or PW) during the Treatment Period and Months 9 and 12 [or PW] of the Follow-Up Period). The dose on Day 1 may be based on the weight determined at the most recent clinic visit, provided the most recent visit was within the prior 3 weeks. The doses on Week 3 through Week 9 are based on the weight determined on Day 1. The weight used in the Week 12 dose calculation can be the weight determined on Day 1 or the weight obtained at Week 12. The weight obtained at Week 12 can be used to adjust the dose beginning at Week 12 or Week 15 through Week 21, as appropriate.

Example 26. ECGs 12-lead ECGs are performed at Baseline, Weeks 3, 6, 12, and 24 (or PW) of the Treatment Period, and Month 12 (or PW) of the Follow-Up Period. At infusion visits, the ECG is performed prior to the infusion. The results are recorded as normal or abnormal on the eCRF and all abnormal results will be evaluated as clinically (CS) or not clinically significant (NCS) by the Investigator. A copy of the ECG tracing remains with the source documents.

Example 27. Immunogenicity Testing

Blood samples are collected in a 5 mL SST collection tube for immunogenicity testing (ADA and possibly Neutralizing Antibodies [NAb]) from all subjects prior to dosing on Day 1, prior to dosing on Weeks 3 and 9, and at Week 24 (or PW) of the Treatment Period, and Months 9 and 12 (or PW) of the Follow-Up Period. Samples are collected, processed, and stored at $\geq-70°$ C. at the site until shipment to the central laboratory (Eurofins Global Central Laboratory). Samples are stored at $\geq-70°$ C. until (transport for) immunogenicity testing. If a subject tests positive for ADA after confirmatory and reactive titer testing, the sample is then tested for NAb. If the subject tests positive for NAb, he/she is followed until levels either revert to Baseline or the subject's value decreases or remains stable. Any subject with a positive NAb test at Month 12 (or EOS) of the follow-up period continues to be followed until the subject's value decreases or remains stable.

Example 28. Study Procedures

Subjects who provide informed consent and who meet all the entry criteria for participation in this study may be enrolled in the open-label extension study.

Day 1/Baseline: The Baseline (Day 1) Visit must occur within 14 days of the final visit of lead-in trial. If Day 1 of the extension study occurs on the same day as the final visit of the lead-in study and an assessment is scheduled for both visits, assessments do not need to be repeated, and the final assessments from the lead-in study will serve as the Baseline assessments for the extension study.

Potential study subjects will be informed fully regarding the nature of the study and possible AEs, and will receive a copy of the informed consent form (ICF) for review. Potential study subjects must read the ICF and sign the document after the investigator has answered all questions to the study candidate's satisfaction. Further procedures begin only after the ICF has been signed. The original signed ICF is retained by the Investigator and a copy will be given to the study subject.

Study candidates are evaluated for study entry according to the stated inclusion and exclusion criteria. The investigator evaluates the results of all examinations, including clinical laboratory tests, from the most recent clinic visit and will determine each candidate's suitability for the study. The investigator reviews these results before determining that a candidate is eligible for study drug treatment. The Baseline urine pregnancy test performed for all female candidates of childbearing potential must be negative in order for subjects to be eligible for treatment. The following procedures are performed at Baseline to establish each candidate's general health and eligibility for enrollment into the study:

Obtain signed, written informed consent and permission to use Protected Health Information (in accordance with the Health Insurance Portability and Accountability Act [HIPAA]). Refusal to provide this permission excludes an individual from eligibility for study participation. Record date informed consent is given and who conducted the process on the appropriate source documentation.

Determine study eligibility through review of the inclusion/exclusion criteria.

Obtain predose blood samples for hematology and chemistry (including thyroid, glucose, and HbA1C) analysis.

Collect predose blood samples for immunogenicity and PK testing.

Collect predose urine sample for urinalysis and also for a pregnancy test for females of childbearing potential; the pregnancy test must be negative for the subject to receive study drug.

Enquire about signs and symptoms within previous 2 weeks.

Enquire about prior medication use during the previous 2 weeks.

Perform predose physical and ophthalmic examinations.

Measure weight.

Perform predose 12-lead ECG.

Perform predose Baseline efficacy assessments (proptosis, CAS, diplopia, Clinical Measures of Severity including motility restriction).

Administer the predose GO-QoL questionnaire.

Register enrollment in EDC, obtain study medication vial assignment, and to determine the volume of study drug to be administered.

Monitor vital signs prior to and at the end of the infusion. Additional vital sign monitoring may be performed in the event of infusion-associated AEs.

Administer the first dose of study drug and record date, volume and rate of infusion, and start/stop times of dosing.

Monitor subjects regarding treatment-emergent signs and symptoms.

Collect blood samples for PK analyses at the end of the infusion.

Subjects are discharged from the study center after all of the Study Day 1 procedures had been completed and are contacted the following day to enquire about AEs and concomitant medication use.

Week 1:

Collect blood samples for hematology and glucose testing.

Perform physical and ophthalmic examinations, including vital signs.

Enquire about AEs and concomitant medication use.

Collect blood sample for PK analyses. Record date/time of sample collection.

Subjects are released from the study center after all of the visit procedures have been completed and are instructed to return to the clinic at Week 3.

Week 3:
  Obtain predose blood samples for hematology and chemistry (including thyroid, glucose, but not HbA1C) analysis.
  Collect predose urine sample for urinalysis and also for a pregnancy test for females of childbearing potential; the pregnancy test must be negative for the subject to receive study drug.
  Collect predose blood sample for immunogenicity and PK testing.
  Enquire about signs and symptoms and concomitant medications throughout the visit.
  Perform predose 12-lead ECG.
  Contact IWRS to obtain study medication vial assignment and to determine volume of study drug to be administered.
  Monitor vital signs prior to and at the end of the infusion. Additional vital sign monitoring may be performed in the event of infusion-associated AEs.
  Administer study drug and record date, volume and rate of infusion, and start/stop times of dosing.
  Collect blood samples for PK analyses at the end of the infusion.

Subjects are discharged from the study center after all of the procedures are completed and are contacted the following day to enquire about AEs and concomitant medication use. Subjects are instructed to return to the clinic at Week 4.

Week 4:
  Collect blood samples for hematology and glucose testing.
  Collect vital signs.
  Enquire about AEs and concomitant medication use.
  Collect blood sample for PK analyses. Record date/time of sample collection.

Subjects are released from the study center after all of the visit procedures are completed and are instructed to return to the clinic at Week 6.

Week 6:
  Obtain predose blood samples for hematology and chemistry (including thyroid, glucose, but not HbA1C) analysis.
  Collect predose urine sample for urinalysis and also for a pregnancy test for females of childbearing potential; the pregnancy test must be negative for the subject to receive study drug.
  Enquire about signs and symptoms and concomitant medications throughout the visit.
  Perform predose 12-lead ECG.
  Perform predose physical and ophthalmic examinations, including vital signs. Additional vital sign monitoring may be performed in the event of infusion-associated AEs.
  Perform predose efficacy assessments (CAS, Clinical Measures of Severity including proptosis, diplopia and motility restriction).
  Administer predose GO-QoL questionnaire.
  Obtain study medication vial assignment and volume of study drug to be administered from EDC.
  Administer study drug and record date, volume and rate of infusion, and start/stop times of dosing.

Subjects are discharged from the study center after all of the procedures are completed and are instructed to return for a clinic visit at Week 9.

Week 9:
  Obtain predose blood samples for hematology and chemistry (including thyroid, glucose, but not HbA1C) analysis.
  Collect predose urine sample for urinalysis and also for a pregnancy test for females of childbearing potential; the pregnancy test must be negative for the subject to receive study drug.
  Collect predose blood samples for immunogenicity and PK testing.
  Enquire about signs and symptoms and concomitant medications throughout the visit.
  Collect predose vital signs. Additional vital sign monitoring may be performed in the event of infusion-associated AEs.
  Obtain study medication vial assignment and volume of study drug to be administered from EDC.
  Administer study drug and record date, volume and rate of infusion, and start/stop times of dosing.
  Collect blood samples for PK analyses at the end of the infusion.

Subjects are discharged from the study center after all of the procedures have been completed and are instructed to return for a clinic visit at Week 12.

Week 12:
  Obtain predose blood samples for hematology and chemistry (including thyroid, glucose, and HbA1C) analysis.
  Collect predose urine sample for urinalysis and also for a pregnancy test for females of childbearing potential; the pregnancy test must be negative for the subject to receive study drug.
  Enquire about signs and symptoms and concomitant medications throughout the visit.
  Perform predose 12-lead ECG.
  Perform predose physical and ophthalmic examinations, including vital signs. Additional vital sign monitoring may be performed in the event of infusion-associated AEs.
  Measure weight.
  Perform predose efficacy assessments (CAS, Clinical Measures of Severity including proptosis, diplopia and motility restriction).
  Administer predose GO-QoL questionnaire.
  Obtain study medication vial assignment and volume of study drug to be administered from EDC.
  Administer study drug and record date, volume and rate of infusion, and start/stop times of dosing.

Subjects are discharged from the study center after all of the procedures are completed and are instructed to return to the clinic at Week 15.

Week 15:
  Obtain predose blood samples for hematology and glucose analysis.
  Perform predose urine pregnancy test for females of childbearing potential; the pregnancy test must be negative for the subject to receive study drug.
  Enquire about signs and symptoms and concomitant medications throughout the visit.
  Collect predose vital signs. Additional vital sign monitoring may be performed in the event of infusion-associated AEs.
  Obtain study medication vial assignment and volume of study drug to be administered from EDC.

Administer study drug and record date, volume and rate of infusion, and start/stop times of dosing.

Subjects are discharged from the study center after all of the procedures are completed and are instructed to return to the clinic at Week 18.

Week 18:
- Obtain predose blood samples for hematology and chemistry (including thyroid, glucose, but not HbA1C) analysis.
- Collect predose urine sample for urinalysis and also for a pregnancy test for females of childbearing potential; the pregnancy test must be negative for the subject to receive study drug.
- Enquire about signs and symptoms and concomitant medications throughout the visit.
- Perform predose physical and ophthalmic examinations, including vital signs. Additional vital sign monitoring may be performed in the event of infusion-associated AEs.
- Perform predose efficacy assessments (CAS, Clinical Measures of Severity including proptosis, diplopia, and motility restriction).
- Obtain study medication vial assignment and volume of study drug to be administered from EDC.
- Administer study drug and record date, volume and rate of infusion, and start/stop times of dosing.

Subjects are discharged from the study center after all of the procedures are completed and are instructed to return to the clinic at Week 21.

Week 21:
- Obtain predose blood samples for hematology and glucose analysis.
- Collect predose urine sample for a pregnancy test for females of childbearing potential. The pregnancy test must be negative for those subjects to receive study drug.
- Enquire about signs and symptoms and concomitant medications throughout the visit.
- Collect predose vital signs. Additional vital sign monitoring may be performed in the event of infusion-associated AEs.
- Obtain study medication vial assignment and volume of study drug to be administered from EDC.
- Administer study drug and record date, volume and rate of infusion, and start/stop times of dosing.

Subjects are discharged from the study center after all of the procedures are completed and are instructed to return to the clinic at Week 24.

Week 24/Premature Withdrawal: the final visit of the Treatment Period. Study drug is not administered.
- Obtain blood samples for hematology and chemistry (including thyroid, glucose, and HbA1C) analysis.
- Collect urine sample for urinalysis and also for a pregnancy test for females of childbearing potential.
- Collect blood sample for immunogenicity testing (only subjects who complete the Treatment Period, not those who prematurely discontinue study drug administration).
- Enquire about signs and symptoms and concomitant medications throughout the visit.
- Perform 12-lead ECG.
- Perform physical and ophthalmic examinations, including vital signs.
- Measure weight.
- Perform efficacy assessments (CAS, Clinical Measures of Severity including proptosis, diplopia, and motility restriction).
- Administer GO-QoL questionnaire.
- Collect blood sample for PK analyses (only subjects who complete the Treatment Period, not those who prematurely discontinue study drug administration).

Subjects who relapsed during the Follow-Up Period of the lead-in study and chose to enter this extension study are discharged from the study following completion of the assessments (they will not participate in the Follow-Up Period). Subjects who were proptosis non-responders in Study the lead-in study will enter the Follow-Up Period and were instructed to return to the clinic in one month for the first follow-up visit.

Month 7—Follow-Up Period:
- Collect urine sample for a pregnancy test for females of childbearing potential.
- Enquire about signs and symptoms and concomitant medications throughout the visit.
- Collect vital signs.
- Perform efficacy assessments (CAS, Clinical Measures of Severity including proptosis, diplopia, and motility restriction).
- Administer GO-QoL questionnaire.

Subjects are discharged from the study center after all of the procedures are completed and are instructed to return to the clinic for the Month 9 Follow-Up Visit.

Month 9—Follow-Up Period:
- Obtain blood samples for hematology and chemistry (including thyroid, glucose, and HbA1C) analysis.
- Collect urine sample for urinalysis and also for a pregnancy test for females of childbearing potential.
- Enquire about signs and symptoms and concomitant medications throughout the visit.
- Collect blood sample for immunogenicity testing.
- Collect vital signs.
- Perform efficacy assessments (CAS, Clinical Measures of Severity including proptosis, diplopia, and motility restriction).
- Measure weight.

Subjects are discharged from the study center after all of the procedures are completed and are instructed to return to the clinic at Month 12.

Month 12/Premature Withdrawal—Follow-Up Period
For Proptosis Non-Responders in Lead-In Study:
- Obtain blood samples for hematology and chemistry (including thyroid, glucose, and HbA1C) analysis.
- Collect urine sample for urinalysis.
- Collect urine sample for a pregnancy test for females of childbearing potential if the subject discontinued from the study prior to Month 9 of the Follow-Up Period.
- Collect blood sample for immunogenicity testing.
- Enquire about signs and symptoms and concomitant medications throughout the visit.
- Perform 12-lead ECG.
- Perform physical and ophthalmic examinations, including vital signs.
- Measure weight.
- Perform efficacy assessments (CAS, Clinical Measures of Severity including proptosis, and motility restriction).
- Administer GO-QoL questionnaire.

For Proptosis Subjects Who Relapsed in Lead-In Study: subjects who complete the Week 24 Visit will be contacted 6 months later via phone or email by research staff to enquire if any treatment for TED has been received since last study contact. If yes, subject will be questioned regarding type of treatment and outcome/response.

Month 18—Follow-Up Period:

For Proptosis Non-responders in Lead-In Study: Subjects who complete the Month 12 Visit will be contacted 6 months later via phone or email by research staff to enquire if any treatment for TED has been received since last study contact. If yes, subject will be questioned regarding type of treatment and outcome/response.

For Subjects Who Relapsed in the Lead-In Study: Subjects who complete the Week 24 Visit will be contacted 12 months later via phone or email by research staff to enquire if any treatment for TED has been received since last study contact. If yes, subject will be questioned regarding type of treatment and outcome/response. This is the final contact for subjects who relapsed in the Lead-In Study.

Month 24—Follow-Up Period: For Proptosis Non-responders in Lead-In Study

Subjects who complete the Month 12 Visit will be contacted 12 months later via phone or email by research staff to enquire if any treatment for TED has been received since last study contact. If yes, subject will be questioned regarding type of treatment and outcome/response. This is the final contact for proptosis non-responders the Lead-In Study. The end of the trial is defined as the date of the last subject contact at Month 24.

Example 29. Statistical Analyses

The primary analyses are conducted on the Intent-to-Treat (ITT) population. All efficacy and safety endpoints are summarized using descriptive statistics, and summaries are stratified by the treatment received in the lead-in trial as well as overall. Study endpoints are evaluated for all subjects from Baseline to the Week 24 Visit. The Clinical Measures of Severity results for each item will be summarized at each designated visit for each eye with the number and percentage of subjects being classified as responders on each individual criterion.

Primary Efficacy Endpoint: The primary outcome measure is the proptosis responder rate (percentage of subjects with a ≥2 mm reduction from Baseline in proptosis in the study eye, without deterioration [≥2 mm increase] of proptosis in the fellow eye) at Week 24.

Secondary Efficacy Endpoints: Secondary efficacy endpoints included:
- the percentage of subjects with a CAS value of 0 or 1 at Week 24;
- the mean changes from Baseline to Week 24 in proptosis the study eye;
- the diplopia responder rate (percentage of subjects with baseline diplopia >0 in study eye who have a reduction of ≥1 grade with no corresponding deterioration [≥1 grade worsening] in the fellow eye) at Week 24; and
- the mean change from Baseline to Week 24 in the GO-QoL questionnaire overall score.

Exploratory Efficacy Endpoints:
- The overall responder rate (percentage of subjects with ≥2-point reduction in CAS AND ≥2 mm reduction in proptosis from Baseline, provided there is no corresponding deterioration [≥2 point/mm increase] in CAS or proptosis in the fellow eye) at Week 24.
- The Clinical Measures of Severity individual response status frequencies and percentage of responders for each component of clinical severity at Week 24.
- The mean change from Baseline to Week 24 in the CAS (CAS will be measured as a continuous variable and will be summarized at each designated visit.).
- The overall responder rate at Week 24 stratified by the level of response (high responders, responders, low responders, and non-responders.
- The mean change from Baseline to Week 24 in the GO-QoL questionnaire VF and A subscale scores.
- The mean change from Baseline to Week 24 on the motility component of the Clinical Measures of Severity.
- Evaluate pharmacokinetic (PK) parameters of teprotumumab to estimate exposure and understand PK-PD relationships.

Example 30. Stratification of Proptosis and CAS Response into Four Responses Categories To further explore the response based on both proptosis and CAS reduction, each subject is classified into one of 4 response categories at Week 24:

High responders: Subjects who have a reduction in both proptosis and CAS of 3 or more (>3) from Baseline in the study eye, and no deterioration in the fellow eye (i.e., increase in CAS≥2 points or increase in proptosis >2 mm).

Responders: Subjects who have a reduction in both CAS and proptosis of 2 or more (but less than 3) from Baseline in the study eye, and no deterioration in the fellow eye.

Low Responders: Subjects who have a reduction in both CAS and proptosis of 1 or more (but less than 2) from Baseline in the study eye, and no deterioration in the fellow eye.

Non-Responders: Subjects who do not fit into any of the above categories, or were not present for the Week 24 evaluation.

Example 31. Pharmacokinetic Measurements

Blood samples are collected in 5 mL serum separator tube (SST) collection tubes to evaluate PK at the following time points: pre- and post-infusion on Day 1 and Weeks 3 and 9 of the Treatment Period; single samples will also be collected at Weeks 1, 4, and 24 (but not PW) of the Treatment Period. Samples are collected, processed, and stored at ≥−70° C. at the site until shipment to a laboratory, where they are stored at ≥−70° C. until PK testing.

Results

It is expected that an antibody, or an antigen binding fragment thereof, that specifically binds to and/or inhibits insulin like growth factor-I receptor (IGF-IR), for example
- one having one or more CDRs chosen from SEQ ID NO.s 1-9,
- one having a heavy chain comprising CDR1, CDR2 and CDR3 and a light chain comprising CDR1, CDR2 and CDR3, from SEQ ID NO.s 1-9,
- one having heavy chain CDR1, CDR2, and CDR3 amino acid sequences and light chain CDR1, CDR2, and CDR3 amino acid sequences are at least 90% identical to (i) the amino acid sequences of SEQ ID NOs: 1-6, respectively; or (ii) the amino acid sequences of SEQ ID NOs: 1, 9, 3, 4, 10, 6,
- one having a heavy chain variable region having at least 80% sequence identity to the amino acid sequence of SEQ ID NO: 7 and a light chain variable region having at least 80% sequence identity to the amino acid sequence of SEQ ID NO: 8,
- one having a heavy chain variable region having at least 80% sequence identity to the amino acid sequence of SEQ ID NO: 11 and a light chain variable region having at least 80% sequence identity to the amino acid sequence of SEQ ID NO: 12,
one having a heavy chain variable region comprising the amino acid sequence of SEQ ID NO: 7 and a light chain variable region comprising the amino acid sequence of SEQ ID NO: 8,
one having a heavy chain variable region comprising the amino acid sequence of SEQ ID NO: 11 and a light chain variable region comprising the amino acid sequence of SEQ ID NO: 12,
antibody 1, or an antigen binding fragment thereof,
or antibody 2, or an antigen binding fragment thereof, or teprotumumab.

will, when administered to a subject with thyroid-associated ophthalmopathy (TAO) who has previously undergone prior treatment (for TAO) with such an antibody, or an antigen binding fragment thereof, and either did not respond to said prior treatment or responded to said prior treatment and later relapsed, effectively:
treat or reduce the severity of thyroid-associated ophthalmopathy (TAO) or a symptom thereof;
reduce proptosis (e.g., by ≥2, 3, 4, or more mm);
reduce CAS (e.g., by ≥2, 3, 4, or 5 points);
not be accompanied by a proptosis deterioration of 2 mm or more in the other (or fellow eye);
improve the subject's quality of life as measured by the GO-QoL, or either of its Functioning or Appearance subscales; and/or
treat or reduce diplopia or the severity of diplopia.

OTHER EMBODIMENTS

The detailed description set-forth above is provided to aid those skilled in the art in practicing the present disclosure. However, the invention described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. In some embodiments, such modifications are also intended to fall within the scope of the appended claims.

Table of Sequences and SEQ ID Numbers

| SEQ ID NO | Description | Sequence |
|---|---|---|
| | Antibody 1 | |
| 1 | CDRH1 aa | Ser Tyr Gly Met His |
| 2 | CDRH2 aa | Ile Ile Trp Phe Asp Gly Ser Ser Thr Tyr Tyr Ala Asp Ser Val Arg Gly |
| 3 | CDRH3 aa | Glu Leu Gly Arg Arg Tyr Phe Asp Leu |
| 4 | CDRL1 aa | Arg Ala Ser Gln Ser Val Ser Ser Tyr Leu Ala |
| 5 | CDRL2 aa | Asp Ala Ser Lys Arg Ala Thr |
| 6 | CDRL3 aa | Gln Gln Arg Ser Lys Trp Pro Pro Trp Thr |
| 7 | VH aa | Gln Val Glu Leu Val Glu Ser Gly Gly Gly Val Val Gln Pro Gly Arg Ser Gln Arg Leu Ser Cys Ala Ala Ser Gly Phe Thr Phe Ser Ser Tyr Gly Met His Trp Val Arg Gln Ala Pro Gly Lys Gly Leu Glu Trp Val Ala Ile Ile Trp Phe Asp Gly Ser Ser Thr Tyr Tyr Ala Asp Ser Val Arg Gly Arg Phe Thr Ile Ser Arg Asp Asn Ser Lys Asn Thr Leu Tyr Leu Gln Met Asn Ser Leu Arg Ala Glu Asp Thr Ala Val Tyr Phe Cys Ala Arg Glu Leu Gly Arg Arg Tyr Phe Asp Leu Trp Gly Arg Gly Thr Leu Val Ser Val Ser Ser |
| 8 | VL aa | Glu Ile Val Leu Thr Gln Ser Pro Ala Thr Leu Ser Leu Ser Pro Gly Glu Arg Ala Thr Leu Ser Cys Arg Ala Ser Gln Ser Val Ser Ser Tyr Leu Ala Trp Tyr Gln Gln Lys Pro Gly Gln Ala Pro Arg Leu Leu Ile Tyr Asp Ala Ser Lys Arg Ala Thr Gly Ile Pro Ala Arg Phe Ser Gly Ser Gly Ser Gly Thr Asp Phe Thr Leu Thr Ile Ser Ser Leu Glu Pro Glu Asp Phe Ala Val Tyr Tyr Cys Gln Gln Arg Ser Lys Trp Pro Pro Trp Thr Phe Gly Gln Gly Thr Lys Val Glu Ser Lys |
| | Antibody 2 | |
| 1 | CDRH1 aa | Ser Tyr Gly Met His |
| 9 | CDRH2 aa | Ile Ile Trp Phe Asp Gly Ser Ser Lys Tyr Tyr Gly Asp Ser Val Lys Gly |
| 3 | CDRH3 aa | Glu Leu Gly Arg Arg Tyr Phe Asp Leu |
| 4 | CDRL1 aa | Arg Ala Ser Gln Ser Val Ser Ser Tyr Leu Ala |
| 10 | CDRL2 aa | Asp Ala Ser Asn Arg Ala Thr |
| 6 | CDRL3 aa | Gln Gln Arg Ser Lys Trp Pro Pro Trp Thr |

-continued

Table of Sequences and SEQ ID Numbers

| SEQ ID NO | Description | Sequence |
|---|---|---|
| 11 | VH aa | Gln Val Gln Leu Val Glu Ser Gly Gly Gly Val Val Gln Pro Gly Arg Ser Leu Arg Leu Ser Cys Ala Ala Ser Gly Phe Thr Phe Ser Ser Tyr Gly Met His Trp Val Arg Gln Ala Pro Gly Lys Gly Leu Glu Trp Met Ala Ile Ile Trp Phe Asp Gly Ser Ser Lys Tyr Tyr Ala Asp Ser Val Lys Gly Arg Phe Thr Ile Ser Arg Asp Asn Ser Lys Asn Thr Leu Tyr Leu Gln Met Asn Ser Leu Arg Ala Asp Asp Thr Ala Val Tyr Tyr Cys Ala Arg Glu Leu Gly Arg Arg Tyr Phe Asp Leu Trp Gly Arg Gly Thr Leu Val Thr Val Ser Ser |
| 12 | VL aa | Glu Ile Val Leu Thr Gln Ser Pro Ala Thr Leu Ser Leu Ser Pro Gly Glu Arg Ala Thr Leu Ser Cys Arg Ala Ser Gln Ser Val Ser Ser Tyr Leu Ala Trp Tyr Gln Gln Lys Pro Gly Gln Ala Pro Arg Leu Leu Ile Tyr Asp Ala Ser Asn Arg Ala Thr Gly Ile Pro Ala Arg Phe Ser Gly Ser Gly Ser Gly Thr Asp Phe Thr Leu Thr Ile Ser Ser Leu Glu Pro Glu Asp Phe Ala Val Tyr Tyr Cys Gln Gln Arg Ser Lys Trp Pro Pro Trp Thr Phe Gly Gln Gly Thr Lys Val Glu Ile Lys |

The invention claimed is:

1. A method of treating thyroid eye disease (TED) in a relapsed subject, the method comprising administering to the relapsed subject an antibody that specifically binds to and inhibits insulin like growth factor-I receptor (IGF IR), and wherein said antibody administered to the relapsed subject is administered by intravenous infusion at a dosage of about 10 mg/kg as a first dose following relapse, and at a dosage of about 20 mg/kg in subsequent doses following relapse,
  wherein the subject has relapsed after a prior treatment regimen with said antibody,
  and wherein said antibody comprises a heavy chain comprising CDRH1, CDRH2, and CDRH3 and a light chain comprising CDRL1, CDRL2, and CDRL3, as set forth in SEQ ID NOs: 1-6, respectively.

2. The method of claim 1, wherein the antibody comprises a heavy chain variable region comprising the sequence of SEQ ID NO: 7 and a light chain variable region comprising the sequence of SEQ ID NO: 8.

3. The method of claim 2, wherein the antibody is a human monoclonal antibody.

4. The method of claim 3, wherein the antibody is teprotumumab.

5. The method of claim 1, wherein the prior treatment regimen comprises intravenous infusion of said antibody in a first dose of about 10 mg/kg and in subsequent doses of about 20 mg/kg.

6. The method of claim 1, wherein the subsequent doses are administered every three weeks for at least 21 weeks.

7. The method of claim 6, wherein the antibody is teprotumumab.

8. The method of claim 1, wherein the relapsed subject has an increase in proptosis of 2 mm or greater in an eye after completion of the prior treatment regimen.

9. The method of claim 1, wherein the relapsed subject has an absolute clinical activity score (CAS) of 4 or greater in an eye after completion of the prior treatment regimen.

10. The method of claim 1, wherein the relapsed subject has a new onset of double vision after completion of the prior treatment regimen.

11. The method of claim 1, wherein the antibody is teprotumumab.

12. The method of claim 1, wherein the relapsed subject has relapsed within 48 weeks after completion of the prior treatment regimen.

13. The method of claim 12, wherein said antibody is teprotumumab, and wherein the prior treatment regimen comprises administration of teprotumumab by intravenous infusion at a first dose of about 10 mg/kg and in subsequent doses of about 20 mg/kg every three weeks, for a total of eight infusions.

14. The method of claim 13, wherein the relapsed subject has relapsed after responding to the prior treatment regimen with teprotumumab, wherein the responding to the prior treatment regimen comprises a reduction of 2 mm or more in proptosis in an eye.

15. The method of claim 1, wherein said antibody is teprotumumab, and wherein administration of teprotumumab to the relapsed subject reduces proptosis by at least 2 mm in an eye and/or reduces the CAS in the subject by at least 2 points.

16. The method of claim 15, wherein administration of teprotumumab to the relapsed subject reduces proptosis by at least 2 mm in an eye.

17. The method of claim 15, wherein administration of teprotumumab to the relapsed subject reduces the CAS in the subject by at least 2 points.

18. The method of claim 1, wherein the relapsed subject has relapsed after responding to the prior treatment regimen, wherein the responding to the prior treatment regimen comprises a reduction of 2 mm or more in proptosis in an eye, and wherein administration of said antibody to the relapsed subject reduces proptosis by at least 2 mm in an eye.

19. A method of treating thyroid eye disease (TED) in a relapsed subject in need thereof comprising:
  a) identifying a subject who has relapsed after responding to a prior treatment regimen with an antibody that specifically binds to and inhibits IGF IR, and wherein the subject is relapsed if the subject meets one or more of the following criteria after completion of the prior treatment regimen:
    (i) an increase in proptosis of 2 mm or greater in an eye;
    (ii) an absolute CAS of 4 or greater in an eye; or
    (iii) a new onset of double vision; and
  b) administering to the relapsed subject identified in a) said antibody, wherein said antibody administered to the relapsed subject is administered by intravenous infusion at a dosage of about 10 mg/kg as a first dose following relapse, and about 20 mg/kg in subsequent doses, and
  wherein said antibody comprises a heavy chain comprising CDRH1, CDRH2, and CDRH3 and a light chain comprising CDRL1, CDRL2, and CDRL3, as set forth in SEQ ID NOs: 1-6, respectively.

20. The method of claim 19, wherein the antibody comprises a heavy chain variable region comprising the sequence of SEQ ID NO: 7 and a light chain variable region comprising the sequence of SEQ ID NO: 8.

21. The method of claim 20, wherein the antibody is a human monoclonal antibody.

22. The method of claim 21, wherein the antibody is teprotumumab.

23. The method of claim 19, wherein the prior treatment regimen comprises intravenous infusion in a first dose of about 10 mg/kg and in subsequent doses of about 20 mg/kg.

24. The method of claim 19, wherein the subsequent doses are administered every three weeks for at least 21 weeks.

25. The method of claim 24, wherein the antibody is teprotumumab.

26. The method of claim 19, wherein the relapsed subject meets the one or more of the criteria within 48 weeks after completion of the prior treatment regimen.

27. The method of claim 26, wherein said antibody is teprotumumab, and wherein the prior treatment regimen with teprotumumab comprises administration of teprotumumab by intravenous infusion in a first dose of about 10 mg/kg and in subsequent doses of about 20 mg/kg every three weeks, for a total of eight infusions.

28. The method of claim 27, wherein responding to the prior treatment regimen with teprotumumab comprises a reduction of 2 mm or more in proptosis in an eye.

29. The method of claim 28, wherein administration of teprotumumab to the relapsed subject reduces proptosis by at least 2 mm in an eye and/or reduces the CAS in the subject by at least 2 points.

30. The method of claim 29, wherein administration of teprotumumab to the relapsed subject reduces proptosis by at least 2 mm in an eye.

31. The method of claim 29, wherein administration of teprotumumab to the relapsed subject reduces the CAS in the subject by at least 2 points.

32. The method of claim 19, wherein said antibody is teprotumumab, and wherein administration of teprotumumab to the relapsed subject reduces proptosis by at least 2 mm in an eye and/or reduces the CAS in the subject by at least 2 points.

33. The method of claim 32, wherein administration of teprotumumab to the relapsed subject reduces proptosis by at least 2 mm in an eye.

34. The method of claim 32, wherein administration of teprotumumab to the relapsed subject reduces the CAS in the subject by at least 2 points.

35. The method of claim 19, wherein the responding to the prior treatment regimen comprises a reduction of 2 mm or more in proptosis in an eye, and wherein administration of said antibody to the relapsed subject reduces proptosis by at least 2 mm in an eye.

36. A method of treating TED in a subject who has relapsed after a prior treatment regimen with teprotumumab, the method comprising:
   administering teprotumumab to a subject who has relapsed after a prior treatment regimen with teprotumumab, by intravenous infusion at a dosage of about 10 mg/kg as a first dose following relapse, and in subsequent doses of about 20 mg/kg, every three weeks,
   wherein the prior treatment regimen comprises administration of teprotumumab by intravenous infusion at a first dose of about 10 mg/kg and in subsequent doses of about 20 mg/kg every three weeks,
   wherein the relapsed subject has relapsed after responding to the prior treatment regimen with teprotumumab,
   wherein the responding to the prior treatment regimen comprises a reduction of 2 mm or more in proptosis in an eye, and
   wherein the administration of teprotumumab to the relapsed subject reduces proptosis by at least 2 mm in an eye and/or reduces the CAS in said subject by at least 2 points.

37. The method of claim 36, wherein administration of teprotumumab to the relapsed subject reduces proptosis by at least 2 mm in an eye.

38. The method of claim 36, wherein administration of teprotumumab to the relapsed subject reduces the CAS in the subject by at least 2 points.

39. The method of claim 36, wherein the relapsed subject meets one or more of the following criteria within 48 weeks after completion of the prior treatment regimen with teprotumumab:
   (i) an increase in proptosis of 2 mm or greater in an eye;
   (ii) an absolute CAS of 4 or greater in an eye; or
   (iii) a new onset of double vision.

* * * * *

UNITED STATES PATENT AND TRADEMARK OFFICE
CERTIFICATE OF CORRECTION

PATENT NO. : 12,358,993 B2  
APPLICATION NO. : 17/531368  
DATED : July 15, 2025  
INVENTOR(S) : David Madden et al.

Page 1 of 1

It is certified that error appears in the above-identified patent and that said Letters Patent is hereby corrected as shown below:

In the Specification

In Column 6, Line 38, delete "3, .i.e., CDR1," and insert --3, i.e., CDR1,--.

In Column 15, Line 48, delete "involvement, .i.e., best-corrected" and insert --involvement, i.e., best-corrected--.

In Column 19, Line 19 (Approx.), delete "on Day1, i.e.," and insert --on Day 1, i.e.,--.

In Column 28, Line 58, delete "aspartate aminotransferase(AST)" and insert --aspartate aminotransferase (AST)--.

In Column 28, Line 58 , delete "≥3 times the" and insert --≤3 times the--.

In Column 28, Line 62, delete "as HgbA1c <9.0%" and insert --as HbA1C <9.0%--.

In Columns 33-34, Line 12, (Table 4), delete "Oral steriod for" and insert --Oral steroid for--.

In Columns 33-34, Line 25, (Table 4), delete "MabThera ® ) or" and insert --MabThera ®) or--.

In Columns 33-34, Line 27, (Table 4), delete "or Roactemra ® )" and insert --or RoActemra ®)--.

In Column 47, Line 67, delete "designated visit.)." and insert --designated visit).--.

In Column 48, Line 50, delete "ID NO.s 1-9," and insert --ID NOs. 1-9,--.

In Column 48, Line 54, delete "ID NO.s 1-9," and insert --ID NOs. 1-9,--.

Signed and Sealed this  
Fourth Day of November, 2025

John A. Squires  
*Director of the United States Patent and Trademark Office*

SEQUENCE LISTING

<160> NUMBER OF SEQ ID NOS: 12

<210> SEQ ID NO 1
<211> LENGTH: 5
<212> TYPE: PRT
<213> ORGANISM: Homo sapiens

<400> SEQUENCE: 1

Ser Tyr Gly Met His
1               5

<210> SEQ ID NO 2
<211> LENGTH: 17
<212> TYPE: PRT
<213> ORGANISM: Homo sapiens

<400> SEQUENCE: 2

Ile Ile Trp Phe Asp Gly Ser Ser Thr Tyr Tyr Ala Asp Ser Val Arg
1               5                   10                  15

Gly

<210> SEQ ID NO 3
<211> LENGTH: 9
<212> TYPE: PRT
<213> ORGANISM: Homo sapiens

<400> SEQUENCE: 3

Glu Leu Gly Arg Arg Tyr Phe Asp Leu
1               5

<210> SEQ ID NO 4
<211> LENGTH: 11
<212> TYPE: PRT
<213> ORGANISM: Homo sapiens

<400> SEQUENCE: 4

Arg Ala Ser Gln Ser Val Ser Ser Tyr Leu Ala
1               5                   10

<210> SEQ ID NO 5

```
<211> LENGTH: 7
<212> TYPE: PRT
<213> ORGANISM: Homo sapiens

<400> SEQUENCE: 5

Asp Ala Ser Lys Arg Ala Thr
1               5

<210> SEQ ID NO 6
<211> LENGTH: 10
<212> TYPE: PRT
<213> ORGANISM: Homo sapiens

<400> SEQUENCE: 6

Gln Gln Arg Ser Lys Trp Pro Pro Trp Thr
1               5                   10

<210> SEQ ID NO 7
<211> LENGTH: 118
<212> TYPE: PRT
<213> ORGANISM: Homo sapiens

<400> SEQUENCE: 7

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser
        115

<210> SEQ ID NO 8
<211> LENGTH: 108
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys
```

```
<210> SEQ ID NO 9
<211> LENGTH: 18
<212> TYPE: PRT
<213> ORGANISM: Homo sapiens

<400> SEQUENCE: 9

Ile Ile Trp Phe Asp Gly Ser Ser Lys Tyr Tyr Gly Asp Ser Val Lys
1               5                   10                  15

Gly Leu

<210> SEQ ID NO 10
<211> LENGTH: 7
<212> TYPE: PRT
<213> ORGANISM: Homo sapiens

<400> SEQUENCE: 10

Asp Ala Ser Asn Arg Ala Thr
1               5

<210> SEQ ID NO 11
<211> LENGTH: 118
<212> TYPE: PRT
<213> ORGANISM: Homo sapiens

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Met
        35                  40                  45

Ala Ile Ile Trp Phe Asp Gly Ser Ser Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Glu Leu Gly Arg Arg Tyr Phe Asp Leu Trp Gly Arg Gly Thr
            100                 105                 110

Leu Val Thr Val Ser Ser
        115

<210> SEQ ID NO 12
<211> LENGTH: 108
<212> TYPE: PRT
<213> ORGANISM: Homo sapiens

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
```

```
            65                  70                  75                  80
Glu Asp Phe Ala Val Tyr Tyr Cys Gln Gln Arg Ser Lys Trp Pro Pro
                    85                  90                  95

Trp Thr Phe Gly Gln Gly Thr Lys Val Glu Ile Lys
                100                 105
```